US006565868B1

(12) United States Patent
Howarth et al.

(10) Patent No.: US 6,565,868 B1
(45) Date of Patent: May 20, 2003

(54) METHODS FOR MICROBIOLOGICAL CONTROL IN AQUEOUS SYSTEMS

(75) Inventors: Jonathan N. Howarth, Baton Rouge, LA (US); Christopher J. Nalepa, Baton Rouge, LA (US); Michael J. Sanders, Baton Rouge, LA (US); David L. Shelton, Baton Rouge, LA (US)

(73) Assignee: Albemarle Corporation, Richmond, VA (US)

( * ) Notice: Subject to any disclaimer, the term of this patent is extended or adjusted under 35 U.S.C. 154(b) by 0 days.

(21) Appl. No.: 09/484,938

(22) Filed: Jan. 18, 2000

(51) Int. Cl.$^7$ .............................................. A01N 25/34

(52) U.S. Cl. .................... 424/408; 424/405; 424/409; 424/420; 424/78.09; 504/150; 504/152; 514/386; 514/389

(58) Field of Search ................................ 424/405, 409, 424/420, 78.09, 408, 76.8; 514/386, 389; 504/150, 152

(56) References Cited

U.S. PATENT DOCUMENTS

| | | | |
|---|---|---|---|
| 2,130,805 A | 9/1938 | Levine | 210/28 |
| 2,392,505 A | 1/1946 | Rogers | 260/309.5 |
| 2,398,598 A | 4/1946 | Rogers | 260/309.5 |
| 2,779,764 A | 1/1957 | Paterson | 260/309.5 |
| 2,795,556 A | 6/1957 | Quinn | 252/187 |
| 2,868,787 A | 1/1959 | Paterson | 260/248 |
| 2,920,997 A | 1/1960 | Wolf et al. | 167/33 |
| 2,971,959 A | 2/1961 | Waugh et al. | 260/309.5 |
| 2,971,960 A | 2/1961 | Waugh et al. | 260/309.5 |
| 3,121,715 A | 2/1964 | Waugh et al. | 260/248 |
| 3,147,259 A | 9/1964 | Paterson | 260/248 |
| 3,345,371 A | 10/1967 | Paterson | 260/192 |
| 3,626,972 A | 12/1971 | Lorenzen | 137/268 |
| 4,078,099 A | 3/1978 | Mazzola | 427/213 |
| 4,119,535 A | * 10/1978 | White et al. | 210/62 |
| 4,126,717 A | 11/1978 | Mazzola | 427/220 |
| 4,136,052 A | 1/1979 | Mazzola | 252/94 |
| 4,199,001 A | 4/1980 | Kratz | 137/268 |
| 4,242,216 A | 12/1980 | Daugherty et al. | 252/103 |
| 4,270,565 A | 6/1981 | King, Sr. | 137/268 |
| 4,293,425 A | 10/1981 | Price | 210/754 |
| 4,327,151 A | 4/1982 | Mazzola | 428/407 |
| 4,331,174 A | 5/1982 | King, Sr. | 137/268 |
| 4,427,692 A | 1/1984 | Girard | 424/273 R |
| 4,451,376 A | * 5/1984 | Sharp | 210/701 |
| 4,465,839 A | 8/1984 | Schulte et al. | 548/310 |
| 4,532,330 A | 7/1985 | Cole | 548/311 |
| 4,537,697 A | 8/1985 | Girard | 252/90 |
| 4,560,766 A | 12/1985 | Girard et al. | 548/311 |
| 4,571,333 A | 2/1986 | Hsiao et al. | 424/22 |
| 4,597,941 A | 7/1986 | Bottom et al. | 422/37 |
| 4,621,096 A | 11/1986 | Cole | 514/389 |
| 4,654,424 A | 3/1987 | Girard et al. | 548/311 |
| 4,659,359 A | 4/1987 | Lorenz et al. | 71/67 |
| 4,662,387 A | 5/1987 | King, Sr. | 137/268 |
| 4,677,130 A | 6/1987 | Puzig | 514/389 |
| 4,698,165 A | 10/1987 | Theyson | 210/755 |
| 4,713,079 A | 12/1987 | Chun et al. | 8/101 |
| 4,728,453 A | 3/1988 | Choy | 252/91 |
| 4,745,189 A | 5/1988 | Lee et al. | 544/221 |
| 4,780,197 A | 10/1988 | Schuman | 210/136 |
| 4,803,079 A | 2/1989 | Hsiao et al. | 424/468 |
| 4,867,895 A | 9/1989 | Choy | 252/91 |
| 4,919,841 A | 4/1990 | Kamel et al. | 252/186.26 |
| 4,925,866 A | 5/1990 | Smith | 514/389 |
| 4,964,892 A | * 10/1990 | Hsu | 71/62 |

(List continued on next page.)

FOREIGN PATENT DOCUMENTS

| | | |
|---|---|---|
| CA | 1230825 | 12/1987 |
| CA | 2042430 | 11/1991 |

(List continued on next page.)

OTHER PUBLICATIONS

Sorum—Fundamentals of General Chemistry p. 315, 1955.*
Al–Zahrani, S.M.; "Utilization of Polyethylene and Paraffin Waxes as Controlled Delivery Systems for Different Fertilizers"; Ind. Eng. Chem. Res., 2000; vol. 39; pp. 369–371.

(List continued on next page.)

Primary Examiner—Neil S. Levy
(74) Attorney, Agent, or Firm—Edgar E. Spielman, Jr.

(57) ABSTRACT

Microbiological control in water systems is achieved with an amount of 1,3-dibromo-5,5-dimethylhydantoin that is less than the amount of N,N'-bromochloro-5,5-dimethylhydantoin required to achieve the same degree of microbiological control. The methods of combating *Escherichia coli* and/or *Enterococcus faecium* in an aqueous medium, and biofilms such as formed by *Pseudomonas aeruginosa* on surfaces contacted by the aqueous medium, involve introducing into the medium a biocidally effective amount of 1,3-dibromo-5,5-dimethylhydantoin. A microbiological control agent for use in water in accordance with U.S. Environmental Protection Agency regulations is purveyed in containers of a water control agent comprising 1,3-dibromo-5,5-dimethylhydantoin, which containers bear a label having thereon dosage levels pursuant to requirements promulgated by the U.S. Environmental Protection Agency. The 1,3-dibromo-5,5-dimethylhydantoin is used or purveyed either as a product having a large average particle size (e.g., 175 microns or more) or in the form of a compacted product. The compacted product can be formed without using a binder where the average particle size of the 1,3-dibromo-5,5-dimethylhydantoin is about 175 microns or more. Alternatively, the compacted product can be formed using a micronized synthetic polyolefin-based hydrocarbon wax and/or a micronized synthetic polyfluorocarbon wax as a binder, provided the wax is compatible with the 1,3-dibromo-5,5-dimethylhydantoin. In this case, the average particle size can be in the range of about 20–600 microns. Similarly, the compacted product can be a product formed from 1,3-dibromo-5,5-dimethylhydantoin having an average particle size of at least 175 microns, using an amount of a saturated, normally solid, fatty amide as the binder.

34 Claims, No Drawings

U.S. PATENT DOCUMENTS

| | | | |
|---|---|---|---|
| 5,076,315 A | 12/1991 | King | 137/268 |
| 5,137,563 A | 8/1992 | Valkanas | 71/64.07 |
| 5,218,983 A | 6/1993 | King | 137/1 |
| 5,338,461 A | 8/1994 | Jones | 210/755 |
| 5,339,889 A | 8/1994 | Bigham | 165/1 |
| 5,384,102 A | 1/1995 | Ferguson et al. | 422/264 |
| 5,403,813 A | 4/1995 | Lichti et al. | 504/116 |
| 5,422,126 A | 6/1995 | Howarth et al. | 424/723 |
| 5,476,116 A | 12/1995 | Price et al. | 137/268 |
| 5,565,109 A | 10/1996 | Sweeny | 210/755 |
| 5,565,576 A | 10/1996 | Hall et al. | 548/317.1 |
| 5,578,559 A | 11/1996 | Dolan et al. | 510/192 |
| 5,591,692 A | 1/1997 | Jones et al. | 504/124 |
| 5,603,941 A | 2/1997 | Farina et al. | 424/405 |
| 5,610,126 A | 3/1997 | Barford et al. | 510/191 |
| 5,614,528 A | 3/1997 | Jones et al. | 514/258 |
| 5,670,451 A | 9/1997 | Jones et al. | 504/134 |
| 5,750,061 A | 5/1998 | Farina et al. | 264/117 |
| 5,753,602 A | 5/1998 | Hung et al. | 510/192 |
| 5,756,440 A | 5/1998 | Watanabe et al. | 510/191 |
| 5,763,376 A | 6/1998 | Ward et al. | 510/191 |
| 5,780,641 A | 7/1998 | Yerushalmi et al. | 548/320.5 |
| 5,859,060 A | 1/1999 | Platt | 514/569 |
| 5,942,153 A | 8/1999 | Heydel | 252/187.33 |
| 5,958,853 A | 9/1999 | Watanabe | 510/192 |
| 5,972,864 A | 10/1999 | Counts | 510/192 |
| 5,981,461 A | 11/1999 | Counts et al. | 510/365 |
| 5,984,994 A | 11/1999 | Hudson | 71/28 |

FOREIGN PATENT DOCUMENTS

| | | |
|---|---|---|
| CA | 2163596 | 9/1996 |
| EP | 0177645 | 4/1986 |
| EP | 0206725 | 12/1986 |
| EP | 0228593 | 7/1987 |
| EP | 0581826 | 9/1995 |
| GB | 1054243 | 1/1967 |
| GB | 1600289 | 10/1981 |
| GB | 2273106 | 6/1994 |
| JP | 56158333 | 12/1981 |
| JP | 7299468 | 11/1995 |
| WO | 8910696 | 11/1989 |
| WO | 9630491 | 10/1996 |
| WO | 9715652 | 5/1997 |
| WO | 9720546 | 6/1997 |
| WO | 9720909 | 6/1997 |
| WO | 9743264 | 11/1997 |
| WO | 9743392 | 11/1997 |
| WO | 0034186 | 6/2000 |

OTHER PUBLICATIONS

Author unknown, "Big Brother Brominator—Brominators", Bulky Systems Website, <http://www.bulkysystemsinc.com/brominator.html> (Visited Aug. 10, 2001). 1 page.

Author unknown, "Bio Lab Brominator", Conely Company Website, <http://www.conelyco.com/Pool-Spa/parts/biobrom.htm> (visited Aug. 10, 2001) 2 pages.

Hayward America's #1 Pool Water Systems Product Catalog, "Automatic Chemical Feeders" Chlorinators (Slow Dissolve Tri–Chlor Only) and Brominators, Hayward Pool Products Inc. Website, <http://www.haywardnet.com/products/catalog/displayProdInfo.cfm?itemID=61>, 2 pages.

Hayward Pool Products Owner's Guide, Installation and Operating Instructions, "Hayward Chemical Feeder", Models C250CF, C500CF, C1100CF, C1800CF, C2400CF,—1998—4 pages.

Hayward America's #1 Pool Water Systems Product Catalog, "Automatic Chemical Feeders" Chlorinators (Slow Dissolve Tri–Chlor Only) and Brominators, Buyers Guide, Hayward Pool Products Inc., Website, <http://www.haywardnet.com/products/catalog/displayProdInfo.cfm?itemID=60>, 2 pg. 2001.

Pentair Pool Products Brochure, "Rainbow Model 320 Automatic Chlorine/Bromine In–line Feeder", Saves Time, Reduces Manual Handling of Chemicals, 7 pages, '99.

Sani–King Spa Feeder Product Brochure Model 740 from King Technology Website, <http://www.kingtechnology.com/spafeeder.htm> Visited (Aug. 10, 2001), 2000, 4 pages.

Sani–King Adjust–A–Flo Product Brochure from King Technology Website <http://www.kingtechnology.com/spafeeder.htm> (visited Aug. 10, 2001), 2000, 1 page.

Sani–King Perform–Max Sanitizers for Inground Pools Product Brochure for Model 940 & 960 from King Technology Website, <http://www.kingtechnology.com/perfermaxIG.htm>, visited Aug. 10, 2001, 1 page.

Sani–King Perform–Max Sanitizers for Above Ground Pools Product Brochure Model 910 & 930 from King Technology Website, <http://www.kingtechnology.com/perfermaxIG.htm>, visited Aug. 10, 2001, 2000, 1 page.

Discount Pool & Spa Supplies, Automatic Chlorinators and Chemical Feeders Website, <http://www.discountpoolsupplies.com/Chemfeeders/> Visited Aug. 10, 2001, 3 pages.

Corral et al., "Substitution in the Hydantoin Ring. III. Halogenation", J. Org. Chem., 1963, vol. 28, ppg. 1100–1104.

Jolles, "General Methods of Bromination", Bromine and its Compounds, 1966, Ernest Benn, London, ppg. 365.

Markish et al., "New Aspects on the Preparation of 1,3–Dibromo–5,5–Dimethylhydantoin", Ind. Eng. Chem. Res. 1995, vol. 34, ppg. 2125–2127.

Orazi et al., "Halogenacion con 3–Bromo–5,5–Dimetil–Hidantoina", Anales Assoc. Quim. Argentina, 1949, vol. 37, ppg. 192–196. (Not translated).

Orazi et al., "Halogenacion Con 1–3–Dibromo–5,5–Dimetil–Hidantoina", Anales Assoc. Quim. Argentina, 1950, vol. 38, ppg. 5–11. (Not translated).

HCAPLUS Abstract of JP 09087684 A2 issued 1997.

HCAPLUS Abstract of JP 07277912 A2 issued 1995.

HCAPLUS Abstract of JP 08027119 A2 issued 1996.

Chowhan et al., "Hardness Increase Induced by Partial Moisture Loss in Compressed Tablets and Its Effect on In Vitro Dissolution", J. Pharm. Sciences, Oct. 1978, vol. 67, No. 10, ppg. 1385–1389.

Krycer et al., "An Evaluation of Tablet Binding Agents Part II. Pressure Binders", Powder Technology, 1983, vol. 34, ppg. 53–56.

Petterson, "N–Halogen Compounds. I. Decomposition of 1,3–Dichloro–5,5–dimethylhydantoin in Water at pH 9", J. Org. Chem., 1959, vol. 24, ppg. 1414–1419.

March, "Advanced Organic Chem.", 1992, $4^{th}$ Edition, ppg. 639–640.

HCAPLUS Abstract of JP 07171576 A2 issued 1995.

HCAPLUS Abstract of JP 08239699 A2 issued 1996.

HCAPLUS Abstract of JP 09227317 A2 issued 1997.

* cited by examiner

METHODS FOR MICROBIOLOGICAL CONTROL IN AQUEOUS SYSTEMS

Commonly-owned application Ser. No.09/484,844, filed Jan. 18, 2000, by some of our colleagues, describes and claims chemical processes from which compositions of the present invention can be formed or derived. Commonly-owned application Ser. No. 09/484,687, filed Jan. 18, 2000, by one of us and some of our colleagues, describes and claims 1,3-dibromo-5,5-dimethylhydantoin particulate solids producible by the processes of application Ser. No. 09/484,844, such solids having unprecedented enhanced properties, and compacted articles made from such particulate solids without use of a binder. Commonly-owned application Ser. No. 09/487,816, filed Jan. 18, 2000, by one, of us and one of our colleagues, relates in part to converting 1,3-dihalo-5,5-dimethylhydantoins into compacted articles using novel binders. Commonly-owned application Ser. No. 09/484,891, filed Jan. 18, 2000, by one of us relates to the compacting of 1,3-dihalo-5,5-dimethylhydantoins other than 1,3-dibromo-5,5-dimethylhydantoin without use of binders, and to the novel compacted forms so produced. Commonly-owned application Ser. No. 09/483,896, filed Jan. 18, 2000, by one of us and one of our colleagues relates to the granulation of small average particle size 1,3-dibromo-5,5-dimethylhydantoin and also to the compaction of such granulated products to form larger-sized articles.

BACKGROUND 1,3-Dihalo-5,5-dialkylhydantoins are effective as biocides for aqueous systems such as industrial cooling water, recreational water, and wastewater.

Widely used for such purposes are N,N'-bromochloro-5,5-dialkylhydantoins. One of the features emphasized for such materials is that in use, the chlorine released from the biocide regenerates active bromine from inactive bromide species formed during the water treatment operation. In other words, the chlorine atom in the initial N,N'-bromochloro-5,5-dialkylhydantoin is in effect regarded as a precursor for additional active bromine for sanitation purposes.

As is well known in the art, a deficiency of chlorine, of hypochlorites, and of certain halogenated organic water-treating agents is the formation, during usage, of undesirable disinfection by-products. These by-products are undesirable both from the standpoint of environmental concerns and also from the standpoint of toxicological considerations.

Another very serious problem in connection with water disinfection is biofilm development. Biofilms are bacterial films which tenaciously adhere to surfaces in contact with water such as heat exchanger surfaces, conduit interiors, filters, and other processing equipment. These films are very undesirable because they can harbor dangerous pathogens, and cause damage to the surfaces to which they have become attached. Moreover, the bacteria form a slime layer of extra-cellular polysaccharide which affords protection to the bacteria and in addition constitute an effective barrier against penetration of biocidal agents used in an attempt to combat such bacteria. In situations where the water is prone to development of calcium carbonate scale, the presence of such gelatinous extra-cellular polysaccharides can result in the formation of layers of scale bonded to the substrate surface by the gelatinous polysaccharides. Polysaccharide films and films of scale bonded by means of polysaccharides can greatly interfere with the operation of heat exchangers by virtue of their insulating characteristics, and can markedly interfere with the functioning of filters and the flow of water through pipes and conduits by virtue of the clogging tendencies of such polysaccharide films.

Thus a need exists for a biocidal agent which is highly effective in providing biocidal control, especially eradication, or at least minimization, of biofilms in water systems, and in addition, a biocidal agent which has the capability of providing such biocidal control even though used at very low concentrations in water.

SUMMARY OF THE INVENTION

This invention involves, inter alia, the surprising discovery that 1,3-dibromo-5,5-dimethylhydantoin when used in treating water achieves the requirements mandated by the U.S. Environmental Protection Agency at a dosage level that is only one-half of that required when using one or a mixture of N,N'-bromochloro-5,5-dialkylhydantoins. This discovery enables the use of extremely small concentrations of the 1,3-dibromo-5,5-dimethylhydantoin to effectively sanitize water while at the same time achieving excellent microbiological control. Further, the ability to effectively utilize such small concentrations is expected to result in significant reduction in formation of disinfection by-products.

Another important facet of this invention is the fact that so far as is presently known, 1,3-dibromo-5,5-dimethylhydantoin has never before been used as the sole disinfecting agent for sanitizing water. Instead, in the prior art, only when in admixture with much larger quantities of N,N'-bromochloro-5,5-dimethylhydantoin was 1,3-dibromo-5,5-dimethylhydantoin deemed suitable for use in water sanitation.

Another totally unexpected benefit resulting from the use of 1,3-dibromo-5,5-dimethylhydantoin in water systems is its exceptional effectiveness in destruction and removal of biofilm. Indeed, 1,3-dibromo-5,5-dimethylhydantoin has been found to be almost twice as effective in biofilm eradication as N,N'-bromochloro-5,5-dimethylhydantoin and even more effective in this regard than a number of other known biocidal agents. Because of such great effectiveness, 1,3-dibromo-5,5-dimethylhydantoin can be effectively utilized for biofilm control at extremely low concentrations. This in turn results in substantial benefits from an environmental standpoint and from the standpoint of operating costs.

More particularly, it has been discovered that in the AOAC Official Method: Disinfectants For Swimming Pools (also referred to as Presumptive Efficacy Test) only 1 milligram of bromine (as $Br_2$) from 1,3-dibromo-5,5-dimethylhydantoin per liter of water satisfies these official requirements for labeling purposes. In sharp: contrast, parallel tests conducted using N,N'-bromochloro-5,5-dimethylhydantoin required 2 milligrams of bromine (as $Br_2$) per liter of water in order to satisfy these official requirements.

Similarly, it has been discovered that in standard tests developed at the University of Calgary for measuring effectiveness in control of biofilms, 1,3-dibromo-5,5-dimethylhydantoin was effective against *Pseudomonas aeruginosa* biofilms at levels as small as 1.4 mg/L (total halogen measured as $Br_2$) whereas levels of at least 2.5 mg/L (total halogen measured as $Br_2$) were required when using N,N'-bromochloro-5,5-dimethylhydantoin.

Accordingly, this invention provides, in one of its embodiments, a method of treating water for microbiological control and/or biofilm eradication, said method comprising introducing into the water to be treated an amount of 1,3-dibromo-5,5-dimethylhydantoin that is far less than the amount of N,N'-bromochloro-5,5-dimethylhydantoin required to achieve the same microbiological control and/or biofilm eradication.

Another embodiment of this invention is the method of combating *Escherichia coli* in an aqueous medium, which method comprises introducing into said medium a biocidally effective amount of 1,3-dibromo-5,5-dimethylhydantoin. This amount is far less than the amount of N,N'-bromochloro-5,5-dimethylhydantoin required to achieve the same level of effectiveness against *Escherichia coli*.

Still another embodiment of this invention is the method of combating *Enterococcus faecium* in an aqueous medium, which method comprises introducing into said medium a biocidally effective amount of 1,3-dibromo-5,5-dimethylhydantoin. This amount is far less than the amount of N,N'-bromochloro-5,5-dimethylhydantoin required to achieve the same level of effectiveness against *Enterococcus faecium*.

A preferred embodiment of this invention is the method of concurrently controlling *Escherichia coli* and *Enterococcus faecium* in an aqueous medium, which method comprises introducing into the aqueous medium a biocidally effective amount of 1,3-dibromo-5,5-dimethylhydantoin. Here again, the amount of 1,3-dibromo-5,5-dimethylhydantoin required to achieve this concurrent control of *Escherichia coli* and *Enterococcus faecium* is much lower than the amount required when utilizing N,N'-bromochloro-5,5-dimethylhydantoin.

A further embodiment of this invention is the method of eradicating or at least reducing *Pseudomonas aeruginosa* biofilm on a surface contacted by an aqueous medium, which method comprises introducing into the aqueous medium, a biocidally effective amount of 1,3-dibromo-5,5-dimethylhydantoin to eradicate or substantially eradicate such biofilm. As noted above, this amount of 1,3-dibromo-5,5-dimethylhydantoin is significantly less than the amount of N,N'-bromochloro-5,5-dimethylhydantoin required to achieve the same effectiveness in removal of such biofilm.

Yet another embodiment of this invention is the method of purveying a microbiological control agent for water in accordance with U.S. Environmental Protection Agency regulations, which method comprises purveying a container of a water control agent comprising 1,3-dibromo-5,5-dimethylhydantoin, said container bearing a label having thereon dosage levels pursuant to requirements promulgated by the U.S. Environmental Protection Agency. Typically, this water control agent will be in a compacted form, such as granules, tablets, briquettes, or pucks.

Other embodiments, features, and advantages of this invention will be still further apparent from the ensuing description and appended claims.

FURTHER DETAILED DESCRIPTION

Among the features of this invention is the fact that the aforementioned compacted forms can be produced and provided in forms devoid of any binder. This unprecedented feature is now possible by virtue of the fact that 1,3-dibromo-5,5-dimethylhydantoin can be produced, for the first time, having an average particle size of at least about 175 microns. Indeed, 1,3-dibromo-5,5-dimethylhydantoin with average particle sizes of at least about 200 microns, at least about 300 microns, and at least about 600 microns can be produced utilizing process technology described in commonly-owned application Ser. No. 09/484,844, filed Jan. 18, 2000. Preparation of the binder-free compacted forms is described in commonly-owned application Ser. No. 09/484,687, filed Jan. 18, 2000. The disclosures of both of these commonly-owned Applications are incorporated in toto herein by reference.

Yet another feature of this invention is that highly-effective forms of 1,3dibromo-5,5-dimethylhydantoin can also be produced with the aid of novel types of binders which result in the formation of compacted products having superior mechanical and physical properties. Preparation of the compacted forms is described in commonly-owned copending application Ser. No. 09/487,816, filed Jan. 18, 2000, the disclosure of which is incorporated, in toto herein by reference.

Pursuant to further embodiments of this invention, it has been found possible to utilize noncompacted forms of 1,3-dibromo-5,5-dimethylhydantoin in the methods of this invention. Making this possible is the discovery that 1,3-dibromo-5,5-dimethylhydantoin can be produced having large average particle size with superior flowability characteristics enabling the product to be readily discharged from containers in which it is packaged. Moreover, the larger average particle sized product offers the consumer the advantage of having a product which is less prone to caking during storage, especially in warm, humid climates, than the more finely-divided 1,3-dihalo-5,5-dimethylhydantoin products heretofore available in the marketplace. Still another advantage of the large average particle size 1,3-dibromo-5,5-dimethylhydantoin is that, during use, the consumer is not exposed to irritating dusts produced when filling dispensing devices or otherwise dispersing or broadcasting the product into the water to be treated. The only presently known method for producing such large average particle size 1,3-dibromo-5,5-dimethylhydantoin is described in commonly-owned copending application Ser. No. 09/484,844, filed Jan. 18, 2000, the disclosure of which has been incorporated herein.

The methods of this invention thus involve use of 1,3-dibromo-5,5-dimethylhydantoin in compacted or in non-compacted forms. When used in compacted forms, the compacted forms can be produced without use of a binder; provided that the average particle size of the 1,3-dibromo-5,5-dimethylhydantoin is at least 175 microns. Alternatively, the compacted forms can be produced with use of a binder. A preferred type of binder for producing such compacted products is a saturated, normally solid, fatty amide as described in U.S. Pat. No. 5,565,576, issued Oct. 15, 1996 to L. K. Hall, J. A. Falter, and T. E. Farina, the disclosure of which patent is incorporated herein in toto as if fully set forth herein. In the practice of this invention such fatty amide binder is used with 1,3-dibromo-5,5-dimethylhydantoin having an average particle size of at least 175 microns. A particularly preferred type of binder for use in producing the compacted forms of 1,3-dibromo-5,5-dimethylhydantoin for use in this invention is a micronized synthetic polyolefin-based hydrocarbon wax and/or a micronized synthetic polyfluorocarbon wax effective to form the compacted product, provided the wax is suitably compatible with the 1,3-dibromo-5,5-dimethylhydantoin. In the practice of this invention with compacted forms of blends of 1,3-dibromo-5,5-dimethylhydantoin with a micronized synthetic polyolefin-based hydrocarbon wax and/or a micronized synthetic polyfluorocarbon wax, the average particle size of the 1,3-dibromo-5,5'-dimethylhydantoin can be in the range of about 20 to about 600 microns, but preferably the average particle size of the 1,3-dibromo-5,5-dimethylhydantoin is in the range of about 175 to about 400 microns, if not even greater.

The amount of 1,3-dibromo-5,5-dimethylhydantoin used in practicing the methods of this invention is a biocidally effective amount, e.g., an amount which is at least sufficient to achieve substantial microbiological control, if not complete microbiological control, in the water being treated and/or substantial biofilm eradication,: if not complete biofilm eradication, from the surfaces in contact with the water system being treated. Typically, dosages of 1,3-dibromo-5,5-dimethylhydantoin used for this purpose will fall within the range of about 0.2 to about 10 milligrams of bromine, as $Br_2$, per liter of water. Preferably, such dosages are in the range of about 0.2 to about. 5 milligrams of bromine, as $Br_2$, per liter of water. However, departures from these ranges are permissible provided that the departures result in sufficient microbiological control in accordance with the needs of the occasion, including applicable governmental regulations.

In order to demonstrate the efficacy of this invention, a series of tests was conducted on our behalf by an independent microbiology and virology; laboratory. One such series of tests, which utilized the AOAC Official Method referred to hereinabove, involved determinations of microbiological control against $E. coli$ bacteria. Another set of tests involved determinations of microbiological control against $E. faecium$. In each case, comparative tests were carried out in the same manner utilizing N,N'-bromochloro-5,5-dimethylhydantoin. Briefly, the test involves exposing a culture of the microorganism to various concentrations of bromine solution prepared from an aqueous stock solution of the compound under test. At various time intervals the bromine in the test suspensions is chemically neutralized, and the amount of viable bacteria remaining is enumerated by plating onto nutrient agar and incubating for 2 days at 37° C. Results are expressed at the $log_{10}$ colony forming units (CFU). The concentration of the compound required to achieve complete kill (i.e., no viable bacteria remain) within 30 seconds is determined in the test and reported to the U.S. Environmental Protection Agency to support the product registration as a disinfectant for swimming pools. Such testing is one of the requirements needed for product registration with the EPA, which in turn enables the product to be purveyed with labeling showing the efficacious dosage level of the product.

Table 1 summarizes the data obtained in the tests using respectively, 1,3-dibromo-5,5-dimethylhydantoin (DBDMH) and N,N'-bromochloro-5,5-dimethylhydantoin (BCDMH) and in which the microorganism in each case was $E. coli$. It can be seen that 1,3-dibromo-5,5-dimethylhydantoin passes the test at one milligram of¹bromine, as $Br_2$, per liter of water, as evidenced by the complete kill within 30 seconds, whereas N,N'-bromochloro-5,5-dimethylhydantoin requires two milligrams of bromine, as $Br_2$, per liter to of water to achieve complete kill within 30 seconds.

TABLE 1

EFFECTIVENESS AGAINST $E. COLI$

| Concentration mg/L as $Br_2$ | Contact Time | $Log_{10}$ CFU Recovered Using DBDMH | $Log_{10}$ CFU Recovered Using BCDMH |
|---|---|---|---|
| 0.5 mg/L | 30 sec | >4.48 | >4.48 |
| | 1 min | 1.70 | 4.46 |
| | 2 min | 0 | 1.65 |
| | 3 min | 0 | 0 |
| | 4 min | 0 | 0 |
| | 5 min | 0 | 0 |
| | 10 min | 0 | 0 |
| 1.0 mg/L | 30 sec | 0 | >4.48 |
| | 1 min | 0 | 0.7 |
| | 2 min | 0 | 0 |
| | 3 min | 0 | 0 |
| | 4 min | 0 | 0 |
| | 5 min | 0 | 0 |
| | 10 min | 0 | 0 |
| 2.0 mg/L | 30 sec | 0 | 0 |
| | 1 min | 0 | 0 |
| | 2 min | 0 | 0 |
| | 3 min | 0 | 0 |
| | 4 min | 0 | 0 |
| | 5 min | 0 | 0 |
| | 10 min | 0 | 0 |

Table 2 summarizes the data obtained in the tests using respectively 1,3-dibromo-5,5-dimethylhydantoin (DBDMH) and N,N'-bromochloro-5,5-dimethylhydantoin (BCDMH) and in which the microorganism in each case was $E. faecium$. Table 2 shows that 1,3-dibromo-5,5-dimethylhydantoin passes the test at one milligram of bromine, as $Br_2$, per liter of water, as evidenced by the complete kill within 30 seconds, whereas N,N'-bromochloro-5,5-dimethylhydantoin requires two milligrams of bromine, as $Br_2$, per liter of water to achieve complete kill within 30 seconds.

TABLE 2

EFFECTIVENESS AGAINST $E. FAECIUM$

| Concentration mg/L as $Br_2$ | Contact Time | $Log_{10}$ CFU Recovered Using DBDMH | $Log_{10}$ CFU Recovered Using BCDMH |
|---|---|---|---|
| 0.5 mg/L | 30 sec | 4.32 | >4.48 |
| | 1 min | 2.36 | 3.53 |
| | 2 min | 0 | 2.63 |
| | 3 min | 0 | 0 |
| | 4 min | 0 | 0 |
| | 5 min | 0 | 0 |
| | 10 min | 0 | 0 |
| 1.0 mg/L | 30 sec | 0 | >4.48 |
| | 1 min | 0 | 2.38 |
| | 2 min | 0 | 0 |
| | 3 min | 0 | 0 |
| | 4 min | 0 | 0 |
| | 5 min | 0 | 0 |
| | 10 min | 0 | 0 |
| 2.0 mg/L | 30 sec | 0 | 0 |
| | 1 min | 0 | 0 |
| | 2 min | 0 | 0 |
| | 3 min | 0 | 0 |
| | 4 min | 0 | 0 |
| | 5 min | 0 | 0 |
| | 10 min | 0 | 0 |

Table 3 summarizes test results performed at MBEC Biofilm Technologies, Inc., Calgary, Canada on the effectiveness of various biocides on biofilm removal. The test procedure, developed at the University of Calgary, utilizes a device which allows the growth of 96 identical biofilms under carefully controlled conditions. The device consists of a two-part vessel comprised of an upper plate containing 96 pegs that seals against a bottom plate. The bottom plate can consist of either a trough (for biofilm growth) or a standard 96-well plate (for biocide challenge). The biofilms develop on the 96 pegs. The device has been used as a general method for evaluating the efficacy of antibiotics and biocides towards biofilms. See in this connection H. Ceri, et al., "The MBEC Test: A New In Vitro Assay Allowing Rapid Screening for Antibiotic Sensitivity of Biofilm", *Proceedings of the ASM,* 1998, 89, 525; Ceri, et al., "Antifungal and Biocide Susceptibility testing of Candida Biofilms using the MBEC Device", *Proceedings of the Interscience Conference on Antimicrobial Agents and Chemotherapy,* 1998, 38, 495; and H. Ceri, et al., "The Calgary Biofilm Device: A New Technology for the Rapid Determination of Antibiotic Susceptibility of Bacterial Biofilms", *Journal of Clinical Microbiology,* 1999, 37, 1771–1776.

Six biocide systems were evaluated using the above test procedure and test equipment. Five of these systems were oxidizing biocides, viz., chlorine.(from NaOCl), halogen (from NaOCl+NaBr), halogen (from BCDMH), bromine (from DBDMH), and chlorine (from trichloroisocyanuric acid), all expressed as bromine as $Br_2$ in mg/L, so that all test results were placed on the same basis. The sixth biocide was glutaraldehyde, a non-oxidizing biocide.

These biocide systems were used to challenge biofilms of *Pseudomonas aeruginosa* (ATCC 15442). This is a Gram (−) bacterium which is ubiquitous in microbiological slimes found in industrial and recreational water systems. See in this connection J. W. Costerton and H. Anwar, "*Pseudomonas aeruginosa:* The Microbe and Pathogen", in *Pseudomonas aeruginosa Infections and Treatment,* A. L. Baltch and R. P. Smith editors, Marcel Dekker publishers, New York, 1994.

In Table 3 the MBEC (minimum biofilm eradication concentration) results presented are for the one-hour biocide contact time used in the test. The values given for the halogen containing biocides are expressed in terms of mg/L of bromine as $Br_2$. The data on the glutaraldehyde is in terms of mg/L as active ingredient. The data indicate that the DBDMH used pursuant to this invention was more effective than any of the other biocides tested under these conditions with an MBEC of 1.4 mg/L of bromine, as $Br_2$. In fact, only slightly more than one-half as much bromine from DBDMH was required to remove the biofilm as compared to the total halogen, expressed as $Br_2$, that was required from BCDMH.

TABLE 3

EFFECTIVENESS AGAINST PSEUDOMONAS AERUGINOSA BIOFILM

| Biocide System | MBEC | MBEC, avg. |
|---|---|---|
| Chlorine (from NaOCl) | 5.0, 2.5 | 3.8 |
| Halogen (from NaOCl + NaBr) | 2.5, 2.5 | 2.5 |
| Halogen (from BCDMH) | 2.5, 2.5 | 2.5 |
| Bromine (from DBDMH) | 1.4, 1.4 | 1.4 |
| Chlorine (from Trichloroisocyanuric acid) | 2.6, 1.3 | 2.0 |
| Glutaraldehyde | 50, 50 | 50 |

EXAMPLE 1

1,3-Dibromo-5,5-dimethylhydantoin granules were used to sanitize a swimming pool over a 61-day period during the summer. The granules were placed in a three pound pool floater obtained from a commercial supplier. The floater was initially charged to maximum capacity, and recharged as necessary. An above-ground, 12,400 gallon vinyl-lined swimming pool equipped with a sand filter was used for the test. The pool was exposed to full sunlight. The water was recirculated between the hours of 7 a.m. and 7 p.m. using a 1.5 HP pump. Halogen levels, pH, and temperature were tested twice daily, once in the morning (8 a.m.) and once in the afternoon (1 p.m.). The bromine level was expressed as chlorine for ease of comparison to the industry standard. To convert such chlorine values into bromine values, the chlorine value should be multiplied by 2.25. The alkalinity level was tested once a day. 5,5-Dimethylhydantoin, bromide ion levels, and calcium hardness concentrations were tested once a week.

Consumption data suggests that 2.5–3.0 lbs/10,000 gallons/week of 1,3-dibromo-dimethylhydantoin granules were adequate in the floater to maintain microbiological control of the pool. Table 4 summarizes the bromine levels reported as free available chlorine and total available chlorine, recorded in the morning over the course of the test. The data from the testing indicate that the granules successfully maintained adequate halogen levels for microbiological control under field conditions.

TABLE 4

| Day of test | Free Available $Cl_2$, mg/L as $Cl_2$ | Total Available $Cl_2$, mg/L as $Cl_2$ |
|---|---|---|
| 1 | 0.12 | 0.18 |
| 2 | 1.07 | 1.1 |
| 5 | 0.92 | 1.62 |
| 8 | 0.28 | 0.43 |
| 11 | 0.50 | 0.72 |
| 15 | 0.46 | 0.70 |
| 18 | 0.51 | 0.66 |
| 23 | 0.84 | 1.11 |
| 26 | 0.96 | 1.36 |
| 30 | 2.97 | 3.85 |
| 33 | 0.72 | 0.84 |
| 37 | 0.11 | 0.12 |
| 40 | 0.70 | 1.42 |
| 43 | 0.8 | 0.86 |
| 45 | 3.0 | 3.5 |
| 46 | 0.13 | 0.14 |
| 50 | 0.01 | 0.04 |
| 52 | 0.05 | 0.1 |
| 53 | 0.45 | 0.61 |
| 54 | 0.2 | 0.39 |
| 58 | 1.61 | 2.25 |
| 59 | 1.28 | 1.57 |
| 61 | 0.14 | 0.18 |

EXAMPLE 2

The effectiveness of 1,3-dibromo-5,5-dimethylhydantoin in microbiological control in cooling tower water was investigated. The cooling tower consisted of two 500-ton units in a crossflow design. The total system-contained volume was 14,000 gallons, and the tower contained medium efficiency film fill. Water from the tower cooled the coils of two 300-ton air conditioners (chillers). The tower typically operated at a pH of about 9.1 and 4 cycles of concentration. Blowdown was controlled by conductivity Make-up water consisted of softened city water and which was of good quality. The make-up water was very low in calcium (<10 mg/L) but high in pH (8.7). The alkalinity was 145 mg/L (as $CaCO_3$), and the silica level was 28 mg/L. The tower employed; a conventional polyphosphate/molybdate/phosphonate program to provide corrosion and deposit control.

The 1,3-dibromo-5,5-dimethylhydantoin was introduced to the water using granules charged to a solid halogen feeder (Neptune model BT-40, Neptune Chemical Pump Co., Inc., Lansdale, Pa.). The field trial lasted 51 days. The tower was slug dosed three times a week with 1,3-dibromo-5,5- dimethylhydantoin. Slug dosing was accomplished by diverting a sidestream of the recirculating water through the feeder containing the granules for about 1 to 5 hours until a total halogen residual of about 0.75 mg/L (as $Cl_2$) was obtained. This biocide program reduced bacterial levels in the bulk water by an average of 2 orders of magnitude, with bacteria levels in the bulk water after the biocide dose ranging from $10^1$ to $10^3$ CFUs/mL. Table 5 summarizes the results of using 1,3-dibromo-5,5-dimethylhydantoin to treat the cooling tower water.

TABLE 5*

|  | Cooling Tower Water | Make-up Water |
|---|---|---|
| Cooling Tower Data |  |  |
| Temperature (return line) | 91° F. | — |
| Temperature (to process) | 83° F. | — |
| ΔT | 8° F. | — |
| Make-up water | 4800 gal/day | — |
| Water Chemistry |  |  |
| Free Halogen Residual (as $Cl_2$), mg/L | 0.79 (range = 1.9–0.00) | 0.05 |
| Total Halogen Residual (as $Cl_2$), mg/L | 0.82 (range = 1.9–0.03) | 0.8 |
| Conductivity, mS/cm | 1.22 | 0.32 |
| pH, units | 9.2 | 8.7 |
| Alkalinity, mg/L as $CaCO_3$ | 480 | 145 |
| Total Hardness, mg/L as $CaCO_3$ | 1 | 3 |
| Silica, mg/L | 100 | 28 |
| Microbiological Tests |  |  |
| Aerobic Bacteria, CFUs/mL | $6 \times 10^0 - 3 \times 10^3$ | $10^0$ |

*This data represents the average of several analyses conducted during the course of the field trial.

In other tests, 1,3-dibromo-5,5-dimethylhydantoin granules were used to sanitize an outdoor spa during the summer. Product was dispensed using various floater devices. Product delivery was somewhat erratic due to design deficiencies of the;:floater devices. Consequently, microbiological control was also somewhat erratic. Use of a different delivery method for the product is expected to provide improved performance.

The most effective presently-known process for producing 1,3-dibromo-5,5-dimethylhydantoin for use in the practice of this invention is described in commonly-owned application Ser. No. 09/484,844, filed Jan. 18, 2000. That process comprises, for example, concurrently feeding (i) an aqueous solution or slurry formed from an inorganic base and 5,5-dimethylhydantoin, and (ii) a brominating agent in proportions such that each nitrogen atom is substituted by a bromine atom, thereby continuously forming product which precipitates in an aqueous reaction mixture. The pH of the mixture is continuously maintained in the range of about 5.5 to about 8.5. Examples 3–13 illustrate that process. In Examples 3–13, pH was monitored by use of a pH meter. In Examples 3–12, bromine was fed using a Cole-Parmer Masterflex computerized drive and Easy-Load® pump head. When conducting the continuous operations of Examples 11 and 12, the resulting slurry was collected manually and intermittently from the bottom of the reactor. Each fraction was collected in a 500 mL flask.

EXAMPLE 3

235 Grams of NaOH (5.85 mol) are dissolved in 1800 g of water, and 375 g of 5,5-dimethylhydantoin (2.93 mol) is added to the NaOH solution. There are 935 g of $Br_2$ (5.85 mol) in the bromine reservoir. A 1-liter jacketed flask into which the $Br_2$ and the 5,5-dimethylhydantoin/NaOH solution are fed is maintained at 25° C. with a cooling bath. The 5,5-dimethylhydantoin/NaOH solution is co-fed to the reaction flask simultaneously with, but separately from, $Br_2$. The feed of the 5,5-dimethylhydantoin/NaOH solution was initiated shortly before (e.g., 3–4 min.) the initiation of the $Br_2$ feed. The feed rate of the 5,5-dimethylhydantoin/NaOH solution is 10 mL/minute, and the feed rate of the $Br_2$ is 1.60–1.70 mL/minute. The reaction mixture is stirred with a mechanical stirrer at a rate of 350–400 rpm. During the reaction, the pH ranged from 7.4 to 7.9. The slurry that forms as the reaction progresses is collected at a rate such that the level of the solution in the reaction flask remains constant. 500 mL fractions of product are collected through the bottom of the reaction flask, in an average time of 30 minutes per fraction. When the 5,5-dimethylhydantoin/NaOH solution feed is finished, 86 g of: $Br_2$ (0.54 mol) remains in the bromine reservoir.

Each product fraction is filtered and washed with three 500 mL portions of water, and the solid is then dried under a stream of nitrogen. The isolated yield of 1,3-dibromo-5,5-dimethylhydantoin is 673 g, a yield of 80% based on 5,5-dimethylhydantoin, or a yield of 89% based on $Br_2$. The active bromine content is at least 99%, as determined by iodometric titration.

EXAMPLE 4

44 Grams of NaOH (1.1 mol) are dissolved in 338 g of water, and 70.4 g of 5,5-dimethylhydantoin (0.55 mol) is added to the NaOH solution. There are 175.1 g of $Br_2$ (1.1 mol) in the bromine reservoir. The reaction flask into which the $Br_2$ and the 5,5-dimethylhydantoin/NaOH solution are fed is maintained at 35° C. with a heating bath. The reaction flask is charged with ~200 mL heel (238 g) of a 1,3-dibromo-5,5-dimethylhydantoin filtrate (mother liquor). The 5,5-dimethylhydantoin/NaOH solution is co-fed to the reaction flask simultaneously with, but separately from, $Br_2$. The reaction mixture is stirred with a mechanical stirrer at a rate of 400 rpm. During the reaction, the pH ranged from 6.9 to 8.2. The reaction temperature stabilized at 37° C. during the 0.5 hour addition time. When the addition of reagents is finished, the orange slurry is filtered at 35° C. and washed with 650 mL of water. The resultant white solid is dried overnight under a stream of nitrogen. The isolated yield of 1,3-dibromo-5,5-dimethylhydantoin is 147.6 g, a yield of 94%, and the active bromine content of the 1,3-dibromo-5,5-dimethylhydantoin is 55.1 wt % (98.6% of the theoretical value), as determined by iodometric titration.

EXAMPLE 5

44 Grams of NaOH (1.1 mol) are dissolved in 338 g of water, and 70.4 g of 5,5-dimethylhydantoin (0.55 mol) is added to the NaOH solution. There are 172.0 g of $Br_2$ (1.07 mol) in the bromine reservoir. The reaction flask into which the $Br_2$ and the 5,5-dimethylhydantoin/NaOH solution are fed is maintained at 67° C. with a heating bath. The reaction flask is charged with ~200 mL heel (238 g) of a 1,3-dibromo-5,5-dimethylhydantoin filtrate (mother liquor). The 5,5-dimethylhydantoin/NaOH solution is co-fed to the reaction flask simultaneously with, but separately from, $Br_2$. The bromine is diluted with nitrogen and fed below the surface of the solution in the reaction flask. The reaction mixture is stirred with a mechanical stirrer at a rate of 400 rpm; the pH ranged from 6.7 to 7.1 during the reaction. During the 0.5 hour addition time, the reaction temperature stabilized at 67° C. When the addition of reagents is finished, the orange slurry is discharged from the reaction flask into a beaker and allowed to cool slowly. The slurry is filtered at ~45° C. and washed with two 500 mL portions of water. The resultant white solid is dried overnight under a stream of nitrogen. The isolated yield of 1,3-dibromo-5,5-dimethylhydantoin is 130.5 g, a yield of ~83%; based on 5,5-dimethylhydantoin, or a yield of ~85 % based on $Br_2$. The active bromine content of the 1,3-dibromo-5,5-dimethylhydantoin is 55.9 wt % (100% of the theoretical value), as determined by iodometric titration. Particle size data on the 1,3-dibromo-5,5-dimethylhydantoin product formed in this operation based on a representative dried sample of the product are summarized in Table 6.

TABLE 6

| Particle Size Category | Particle Size of Product |
| --- | --- |
| Average | 237.5 $\mu$ |
| 10% is greater than | 371.6 $\mu$ |
| 25% is greater than | 309.8 $\mu$ |
| 50% is greater than | 239.1 $\mu$ |
| 75% is greater than | 165.6 $\mu$ |
| 90% is greater than | 99.81 $\mu$ |
| Range | 0.040–541.9 $\mu$ |

EXAMPLE 6

354 Grams of NaOH (8.85 mol) are dissolved in 2700 g of water. 562 g of 5,5-dimethylhydantoin (4.386 mol) is added to the NaOH solution. The reaction flask is charged with 500 mL heel of a 1,3-dibromo-5,5-dimethylhydantoin filtrate (mother liquor). The 5,5-dimethylhydantoin/NaOH solution is co-fed to the jacketed reaction flask, no heating or cooling is applied simultaneously with, but separately from, $Br_2$. The feed rate of the 5,5-dimethylhydantoin/NaOH solution is 10 mL/minute, and the feed rate of the $Br_2$ is initially 1.70 mL/minute, but is adjusted later to 1.68 mL/minute to maintain the pH of the reaction mixture at ~7.0. The reaction mixture is stirred with a mechanical stirrer at a rate of 400 rpm reaction temperature is stabilized at about 42° C. The slurry that forms as the reaction progresses is collected at a rate such that the level of the solution in the reaction flask remains constant. Eight 500 mL fractions of product were collected through the bottom of the reaction flask, in an average time of 30 minutes per fraction. A total of 1374.5 g of $Br_2$ (8.59 mol) are added during the reaction.

Each product fraction is filtered and washed with a 500 mL portion of water; the solids are then dried overnight at 50° C. in a vacuum oven. The total isolated yield of 1,3-dibromo-5,5-dimethylhydantoin is 1152 g, a yield of 92% based on 5,5-dimethylhydantoin, or a yield of 94% based on $Br_2$. The active bromine content of the 1,3-dibromo-5,5-dimethylhydantoin ranges from 55.4 wt % to 55.7 wt % (99.1% to 99.7% of the theoretical value), as determined by iodometric titration. The average particle size of the 1,3-dibromo-5,5-dimethylhydantoin is greater than 150$\mu$.

EXAMPLE 7

89 Grams of NaOH (2.2 mol) are dissolved in 676 g of water, and 141 g of 5,5-dimethylhydantoin (1.1 mol) is added to the NaOH solution. There are 350 g of $Br_2$ (2.2 mol) in the bromine reservoir. The reaction flask into which the $Br_2$ and the 5,5-dimethylhydantoin/NaOH solution are fed is maintained at 67° C. with a heating bath. The reaction flask is charged with ~400 mL heel (483 g) of a 1,3-dibromo-5,5-dimethylhydantoin filtrate (mother liquor). The 5,5-dimethylhydantoin/NaOH solution is co-fed to the reaction flask simultaneously with, but separately from, $Br_2$. The reaction mixture is stirred with a mechanical stirrer at a rate of 400 rpm. During the reaction, the pH ranged from 6.8 to 7.1. The reaction temperature stabilized at 67 ° C. during the 66 minute addition time. When the addition of reagents is finished, the orange slurry is filtered at 43° C. and washed with 1000 mL (2×500 mL) of water. The resultant white solid is dried overnight under a stream of nitrogen. 307.3 Grams of Br (1.92 mol) had been fed to the reaction flask. The isolated yield of 1,3-dibromo-5,5-dimethylhydantoin is 212.5 g, a yield of 77% based on $Br_2$, and 68% based on 5,5-dimethylhydantoin; the active bromine content of the 1,3-dibromo-5,5-dimethylhydantoin is 55.9 wt % (100% of the theoretical value), as determined by iodometric titration.

EXAMPLE 8

88 Grams of NaOH (2.2 mol) are dissolved in 338 g of water, and 140.8 g of 5,5-dimethylhydantoin (1.1 mol) is added to the NaOH solution. There are: 352 g of $Br_2$ (2.2 mol) in the bromine reservoir. The reaction flask into which the $Br_2$ and the 5,5-dimethylhydantoin/NaOH solution are fed is maintained at 69° C. with a heating bath. The reaction flask is charged with ~200 mL heel (240 g) of a 1,3-dibromo-5,5-dimethylhydantoin filtrate (mother liquor). The 5,5-dimethylhydantoin/NaOH solution is co-fed to the reaction flask simultaneously with, but separately from, $Br_2$. The reaction mixture is stirred with a mechanical stirrer at a rate of 400 rpm. During the reaction, the pH ranged from 6.8 to 7.0. The reaction temperature stabilized at 68–69° C. during the 39 minute addition time. When the addition of reagents is finished, the orange slurry is filtered at 40° C. and washed with 500 mL of water. The resultant white solid is dried overnight under a stream of nitrogen. 285.5 Grams of $Br_2$ (1.78 mol) had been fed to the reaction flask. The isolated yield of 1,3-dibromo-5,5-dimethylhydantoin is 186.8 g, a yield of 73% based on $Br_2$, and 60% based on 5,5-dimethylhydantoin; the active bromine content of the 1,3-dibromo-5,5-dimethylhydantoin is 53.4 wt % (96% of the theoretical value), as determined by iodometric titration.

Table 7 summarizes the particle size data for the products of Examples 7 and 8.

TABLE 7

| Particle Size Category | Particle Size of Product- Example 7 | Particle Size of Product- Example 8 |
| --- | --- | --- |
| Average | 210.4 $\mu$ | 293.6 $\mu$ |
| 10% is greater than | 381.7 $\mu$ | 451.2 $\mu$ |
| 25% is greater than | 298.3 $\mu$ | 349.6 $\mu$ |
| 50% is greater than | 196.8 $\mu$ | 256.3 $\mu$ |
| 75% is greater than | 115.3 $\mu$ | 174.9 $\mu$ |
| 90% is greater than | 56.86 $\mu$ | 110.6 $\mu$ |
| Range | 0.040–594.9 $\mu$ | 0.040–>2000 $\mu$ |

EXAMPLE 9

44.2 Grams of NaOH (1.1 mol) are dissolved in 338 g of water, and 70.4 g of 5,5-dimethylhydantoin (0.55 mol) is added to the NaOH solution. There are 173 g of $Br_2$ (1.08 mol) in the bromine reservoir. The reaction flask into which the $Br_2$ and the 5,5-dimethylhydantoin/NaOH solution are fed is maintained at 57° C. with a heating bath. The reaction flask is charged with ~200 mL heel (244 g) of a 1,3-dibromo-5,5-dimethylhydantoin filtrate (mother liquor). The 5,5-dimethylhydantoin/NaOH solution is co-fed to the reaction flask simultaneously with, but separately from, $Br_2$. The reaction mixture is stirred with a mechanical stirrer at a rate of 400 rpm. During the reaction, the pH ranged from 6.8 to 7.2. Maintenance of the desired pH was accomplished by adjusting the bromine feed rate. The reaction temperature stabilized at 57° C. during the 33 minute addition time. When the addition of reagents is finished, the orange slurry is filtered at 38° C. and washed with 500 mL of water. The resultant white solid is dried overnight under a stream of nitrogen. The isolated yield of 13-dibromo-5,5-dimethylhydantoin is 139.8 g, a yield of 91% based on $Br_2$, and 89% based on 5,5-dimethylhydantoin; the active bromine content of the 1,3-dibromo-5,5-dimethylhydantoin is 55.7 wt % (99.7% of the theoretical value), as determined by iodometric titration.

EXAMPLE 10

44.2 Grams of NaOH (1.1 mol) are dissolved in 338 g of water, and 70.3 g of 5,5-dimethylhydantoin (0.55 mol) is added to the NaOH solution. There are 172.5 g of $Br_2$ (1.08 mol) in the bromine reservoir. The reaction flask into which the $Br_2$ and the 5,5-dimethylhydantoin/NaOH solution are fed is maintained at 48° C. with a heating bath. The reaction flask is charged with 200 mL heel of a 1,3-dibromo-5,5-dimethylhydantoin filtrate (mother liquor). The 5,5-dimethylhydantoin/NaOH solution is co-fed to the reaction flask simultaneously with, but separately from, $Br_2$. The reaction mixture is stirred with a mechanical stirrer at a rate of 400 rpm. During the reaction, the pH ranged from 6.8 to 7.2. Maintenance of the desired pH was accomplished by adjusting the bromine feed rate. The reaction temperature stabilized at 48° C. during the 34 minute addition time. When the addition of reagents is finished, the orange slurry is filtered at 38° C. and washed with 500 mL of water. The resultant white solid is dried overnight under a stream of nitrogen. The isolated yield of 1,3-dibromo-5,5-dimethylhydantoin is 144.8 g, a yield of 94% based on $Br_2$, and 92% based on 5,5-dimethylhydantoin; the active bromine content of the 1,3-dibromo-5,5-dimethylhydantoin is 55.0 wt %: (98.4% of the theoretical value), as determined by iodometric titration.

The particle size data for the products of Examples 9 and 10 are summarized in Table 8.

TABLE 8

| Particle Size Category | Particle Size of Product-Example 9 | Particle Size of Product-Example 10 |
|---|---|---|
| Average | 231.2 μ | 178.4 μ |
| 10% is greater than | 338.3 μ | 281.1 μ |
| 25% is greater than | 285.0 μ | 230.9 μ |
| 50% is greater than | 228.8 μ | 175.7 μ |
| 75% is greater than | 177.8 μ | 125.0 μ |
| 90% is greater than | 133.0 μ | 79.14 μ |
| Range | 0.040–493.6 μ | 0.040–409.6 μ |

EXAMPLE 11

The process of this Example was conducted in a continuous fashion. A feed solution of 5,5-dimethylhydantoin/NaOH was formed by adding 5,5-dimethylhydantoin to a 9 wt % NaOH solution, such that the 5,5-dimethylhydantoin concentration was about 1.1 M. The 5,5-dimethylhydantoin/NaOH solution was co-fed to the reaction flask simultaneously with, but separately from, $Br_2$. The flask was suspended in a heating bath. The reaction mixture was stirred with a mechanical stirrer at a rate of 500 rpm. The reaction mixture was maintained at a pH of about 7.0±0.2, and the reaction temperature was maintained at 55° C. Ten fractions of product were collected in an: average time of 30 minutes per fraction. The isolated yield of the 1,3-dibromo-5,5-dimethylhydantoin was 90% based on 5,5-dimethylhydantoin, and 92% based on added $Br_2$. The purity of the 1,3-dibromo-5,5-dimethylhydantoin, a white crystalline product, was 99.8%, based on the theoretical bromine content. Fractions 5–10 represent the particle size of the product as formed during steady-state operating conditions. Table 9 summarizes average particle size data and particle size distribution data relating to fractions 5–10 based on samples of each such fraction taken during the steady-state operation of the continuous process. The determinations showed that a bimodal distribution of the product had been produced. The overall average particle size of the product was 512.3 microns.

TABLE 9

| Particle Size | Fraction 5 | Fraction 6 | Fraction 7 | Fraction 8 | Fractions 9 + 10 |
|---|---|---|---|---|---|
| Average | 371.7μ | 445.6μ | 535.5μ | 560.3μ | 545.9μ |
| 10% is greater than | 530.7μ | 626.0μ | 724.7μ | 805.0μ | 952.1μ |
| 25% is greater than | 462.2μ | 550.9μ | 643.3μ | 729.3μ | 833.4μ |
| 50% is greater than | 386.0μ | 474.5μ | 559.7μ | 641.8μ | 676.7μ |
| 75% is greater than | 256.8μ | 369.6μ | 447.8μ | 436.1μ | 149.6μ |
| 90% is greater than | 94.76μ | 134.4μ | 150.3μ | 94.5μ | 76.02μ |
| Range | 0.791–786.9μ; 1255–1512μ | 4.241–786.9μ; 1143–1255μ | 3.519–863.9μ; 1143–1512μ | 3.519–8.639μ; 1143–1512μ | 0.721–409.6μ; 493.6–1255μ |

EXAMPLE 12

Another continuous operation was conducted in a manner similar to that of Example 11. The feed solution was formed by dissolving 355 g (8.87 mols) in 3550 g of water. To this was added 560 g (4.37 mols) of 5,5-dimethylhydantoin. The concurrent feeds were adjusted to maintain the pH of the aqueous reaction mixture at 7.0±0.2. The temperature was maintained at 55° C. The total amount of bromine ($Br_2$) fed was 1359.4 g (8.50 mols). As in Example 11, ten fractions of the reaction mixture were collected. However, in this operation, the addition rates were adjusted such that the average residence time was approximately 1 hour per fraction. The total isolated yield of 1,3-dibromo-5,5-dimethylhydantoin was 88% based on 5,5-dimethylhydantoin used and 90% based on the added bromine. The 1,3-dibromo-5,5-dimethylhydantoin product was obtained as a white crystalline solid. Table 10 summarizes the average particle size data and product distribution data relating to the product formed in this reaction. Fractions 5–10 represent the particle size of the product as formed during steady-state operating conditions. As in Example 11, the product formed was bimodal. In Table 10 "n.d." indicates that the particle size determination for the larger particle sized fraction was not determined; the instrument used could not measure particles having a particle size greater than 2000 microns. The overall average particle size of the product was at least 455.5 microns.

TABLE 10

| Particle Size | Fraction 5 | Fraction 6 | Fraction 7 | Fraction 8 | Fractions 9 + 10 |
|---|---|---|---|---|---|
| Average | 421.2μ | 478.6μ | 494.0μ | 536.6μ | 631.9μ |
| 10% is greater than | 606.5μ | 699.1μ | 781.7μ | 1063μ | 1438μ |
| 25% is greater than | 532.1μ | 623.4μ | 681.5μ | 813.9μ | 995.7μ |
| 50% is greater than | 452.3μ | 535.0μ | 548.5μ | 546.7μ | 522.8 |
| 75% is greater than | 340.0μ | 372.2μ | 176.6μ | 150.3μ | 160.7μ |
| 90% is greater than | 140.8μ | 112.8μ | 68.94μ | 72.93 | 81.68μ |
| Range | 2.423–786.9μ; n.d. | 2.423–863.9μ; n.d. | 1.520–863.9μ; 1255–1512μ | 0.04–2000μ; n.d. | 0.04–>2000μ; n.d. |

EXAMPLE 13

Another continuous operation was performed using a glass reactor into which were concurrently fed, on a continuous basis, an aqueous solution formed from 5,5-dimethylhydantoin and NaOH, and a separate feed of bromine. The aqueous solution was made by adding 5,5-dimethylhydantoin to an aqueous 9 wt % NaOH, solution. This solution contained about 22.4 wt % of 5,5-dimethylhydantoin and 7 wt % NaOH. A one liter, jacketed reactor having an interior diameter of 82 millimeters equipped with an anchor agitator, with an outer diameter of 72 millimeters, was used, and a silicone fluid (Rhodersil 4720V20 fluid; Rhone-Poulenc) was circulated through the jacketing. The temperature of the reaction was controlled at 38° C. Both feeds were controlled by pumps; the average feed rate of the 5,5-dimethylhydantoin/NaOH solution was 15.84 grams/minute via a Prominent Gamma G/4A positive displacement pumps, and the average feed rate of the bromine was 4.67 grams/minute via a Masterflex Easy-Load peristaltic pump. The reaction mixture was stirred at 400 rpm. The pH of the reaction was monitored by measuring the pH of the effluent using a pH meter, and the pH ranged from 6.06 to 6.36 during the reaction. Product removal from the reactor was also controlled by a pump. Residence time was, on average, 30 minutes per fraction; each fraction was about 500 mL. A yield of 90.5% of 1,3-dibromo-5,5-dimethylhydantoin was obtained, based on the amount of 5,5-dimethylhydantoin fed to the reactor. The active bromine content of the 1,3-dibromo-5,5-dimethylhydantoin was >55.3%, as determined by standard iodometric titration. Thus, the purity of this product was greater than 99.0%.

Table 11 summarizes particle size data on the 1,3-dibromo-5,5-dimethylhydantoin product formed in the continuous operation of Example 13. These data are averaged data based on two samples taken at different times during the continuous operation once steady state conditions, or essentially steady state conditions, had been achieved.

TABLE 11

| Particle Size Category | Particle Size of Product |
|---|---|
| Average | 188.9 μ |
| 10% is greater than | 295.2 μ |
| 25% is greater than | 255.6 μ |
| 50% is greater than | 203.1 μ |
| 75% is greater than | 122.5 μ |
| 90% is greater than | 55.9 μ |
| Range | 0.872–356.5 μ |

Examples 14 and 15 illustrate methods of producing tablets from large average particle size 1,3-dibromo-5,5-dimethylhydantoin without use of binders, and the exceptional crush strength of such binder-free tablets. Example 16 illustrates the excellent flowability characteristics and low-dusting properties possessed by the large average particle size 1,3-dibromo-5,5-dimethylhydantoin.

EXAMPLE 14

Five gram samples of 1,3-dibromo-5,5-dimethylhydantoin produced by the process referred to above were compacted without binder in a Sintech® press (MTS Systems Corporation, Edenprairie, Minn.) equipped with a punch and die fabricated from Hastelloy® C alloy. Prior to filling the die, the interior surfaces of the die were lightly dusted with a micronized polypropylene wax (MICROPRO 400 wax; Micro Powders, Incorporated, Tarrytown, N.Y.) to serve as a lubricant. The pressure applied was 5000 psi with no dwell time, i.e., the pressure was automatically terminated immediately upon reaching 5000 psi. The resultant tablets after removal from the die were aged for 6 days at room temperature. Thereupon the tablets were subjected to crush strength testing utilizing a Sintech® 1/S compression apparatus (MTS Systems Corporation, Edenprairie, Minn.) equipped with Testworks software, which software is installed in the 1/S compression apparatus as supplied by MTS Systems Corporation. The apparatus includes a horizontal circular-shaped load cell interfaced with a computer, a digital micrometer also interfaced with the computer, and a vertical screw-driven piston that is disposed above the load cell and adapted to apply a downward force perpendicular to the load cell. The procedure for measuring crush strength involves measuring the thickness of the tablet with the micrometer to provide a digitized input to the computer. Next the tablet is placed on its edge on the load cell with the piston in contact with the upper edge of the tablet. Then the apparatus is activated whereby the piston commences applying a progressively increasing downward diametral force to the tablet. At the same time, the load cell continuously measures the downward force being applied to the tablet, and the input of such measurements is transmitted to the computer. When the force being applied reaches the point where the amount of force suddenly decreases to 10% of the immediately preceding force, the tablet has reached the breaking point, and the application of the force is immediately terminated by the software program. From the inputs to the computer, two values are provided, namely the pounds of force at the breaking point of the tablet, and the pounds of force per inch thickness of the tablet at the breaking point. Thus the greater the force applied, the greater the strength. Two groups of such tests were conducted. One set (Set A) involved forming and evaluating 5 tablets from a batch of 1,3-dibromo-5,5-dimethylhydantoin produced in a continuous process described in Example 12. The other set (Set B) of tests involved 3 tablets produced from another batch of 1,3-dibromo-5,5-dimethylhydantoin produced in a batch process of the type described in Example 8. Table 12 summarizes the results of these tests.

TABLE 12

| Test Set | Tablet Thickness | Crush Strength | Crush Strength |
|---|---|---|---|
| A | 0.365 in. | 20.9 lb. | 57.3 lb./in. |
| A | 0.367 in. | 25.5 lb. | 69.5 lb./in. |
| A | 0.366 in. | 19.2 lb. | 52.5 lb./in. |
| A | 0.367 in. | 22.8 lb. | 62.1 lb./in. |
| A | 0.364 in. | 23.7 lb. | 65.0 lb./in. |
| Avg. of A | — | 22.4 lb. | 61.3 lb./in. |
| B | 0.353 in. | 10.7 lb. | 30.4 lb./in. |
| B | 0.352 in. | 12.8 lb. | 36.4 lb./in. |
| B | 0.354 in. | 9.8 lb. | 27.8 lb./in. |
| Avg. of B | — | 11.1 lb. | 31.5 lb./in. |

Tablets of conventional, small particle sized 1,3-dibromo-5,5-dimethylhydantoin devoid of binder cannot be tableted in the manner described above.

EXAMPLE 15

The crush strength of tablets formed from 1,3-dibromo-5,5-dimethylhydantoin formulated with a binder was illustrated in a group of tests conducted: as described in Example 14. The procedure for producing the tablets was as follows: 1,3-dibromo-5,5-dimethylhydantoin produced as in Example 13 was hand-mixed with 3% by weight of micronized polyethylene wax from Micro Powders Incorporated, Tarrytown, N.Y. for approximately 30 minutes. The resultant formulation was then converted into tablets as described in Example 14. The results of the crush strength tests, conducted as described in Example 14, are summarized in Table 13.

TABLE 13

| Tablet Thickness | Crush Strength | Crush Strength |
|---|---|---|
| 0.372 in. | 39.8 lb. | 107.2 lb./in. |
| 0.375 in. | 44.9 lb. | 119.9 lb./in. |
| 0.375 in. | 37.5 lb. | 100.0 lb./in. |
| 0.375 in. | 36.1 lb. | 96.5 lb./in. |
| 0.377 in. | 37.6 lb. | 99.7 lb./in. |
| Averaged Results | 39.2 lb. | 104.6 lb./in. |

EXAMPLE 16

Comparative flowability tests were carried out using a sample of 1,3-dibromo-5,5-dimethylhydantoin and samples of commercially-available 1,3-dihalo-5,5-dimethylhydantoin products. These tests involved filling an 8-ounce glass jar to about one-third of its capacity with the sample to be tested. After closing the jar, it was slowly rotated while on its side in a single direction while observing the characteristics of the contents. Table 14 summarizes the observations made in these flowability tests. In Table 14 the following abbreviations are used:

DBDMH is 1,3-dibromo-5,5-dimethylhydantoin
DCDMH is 1,3-dichloro-5,5-dimethylhydantoin
BCDMH is N,N'-bromochloro-5,5-dimethylhydantoin

TABLE 14

| N,N'-dihalohydantoin | Average Particle Size | Source | Product Characteristics |
|---|---|---|---|
| DCDMH | 108.1 microns | Aldrich Chemical Co. | Bridging occurred; high dusting, non-free-flowing powder |
| BCDMH | 323.8 microns | Aldrich Chemical Co. | Bridging occurred; high dusting, non-free-flowing powder |
| DBDMH | 162.1 microns | Aldrich Chemical Co. | Bridging occurred; high dusting, non-free-flowing powder |
| DBDMH | 64.5 microns | Albemarle Corporation | Bridging occurred; high dusting, non-free-flowing powder |
| DBDMH | 45.2 microns | Great Lakes Chemical Corporation | Bridging occurred; high dusting, non-free-flowing powder |
| DBDMH | 293.6 microns | The new process of Application No. 09/484,844 | No bridging occurred; low dusting, free-flowing powder |

Examples 17–25 illustrate the preparation and properties of compacted products formed from 1,3-dibromo-5,5-dimethylhydantoin utilizing novel binders as described in commonly-owned application Ser. No. 09/487,816.

EXAMPLE 17

2.5 Grams of a micronized polyethylene wax (MPP-611, Micro Powders Inc., Tarrytown, N.Y.), was weighed into a crystallizing dish, followed by 1,3-dibromo-5,5-dimethylhydantoin (47.5 g). A broad-bladed spatula was used to blend the mixture rather like a cook might blend butter into flour. After 10 minutes of hand mixing in this fashion, the product was admitted to a glass bottle which was rolled to assess the flowability of the mixture. The flow properties were improved over the properties of the 1,3-dibromo-5,5-dimethylhydantoin used to make the blend.

EXAMPLE 18

2.5 Grams of polypropylene wax (MICROPRO 400, Micro Powders Inc., Tarrytown, N.Y.), was weighed into a crystallizing dish, followed by 1,3-dibromo-5,5-dimethylhydantoin (47.5 g). This mixture was blended as described in Example 17, and transferred to a glass bottle which was rolled to assess the flowability of the blend. Its flow properties were improved over the properties of the 1,3-dibromo-5,5-dimethylhydantoin used to make the blend.

EXAMPLE 19

The 1,3-dibromo-5,5-dimethylhydantoin blends prepared in Examples 17 and 18 were subjected to a compaction test. Each sample was weighed, and introduced into a 0.71 inch diameter die made from Hastelloy® C alloy and compacted with a screw-driven punch, also made of Hastelloy® C alloy, to a pre-set pressure. Before filling the die, its interior surfaces were lightly dusted with micronized polypropylene wax to serve as a lubricant. There was no dwell time upon attaining the compaction pressure (the pressure was released immediately). Upon extracting the tablet from the die, the thickness of the tablet was measured with a micrometer, and a visual observation of the tablet was made.

For comparison, the blends were compared to unblended, virgin, commercially produced 1,3-dibromo-5,5-dimethylhydantoin powder with an average particle size of about 64.5µ, and a commercial toilet bowl product (abbreviated in Table 15 as CTB product), which is known to be a mixture of other halogenated hydantoin compounds.

This toilet bowl puck was purchased from a supermarket and ground to a powder with a mortar and pestle, and recompacted as above described.

Table 15 lists the experimental conditions and the observations.

TABLE 15

| Blend | Amount of blend added to die | Pressure | Tablet thickness | Observations |
|---|---|---|---|---|
| DBDMH/5 wt % MPP-611 | 5.0 g | 5000 psi | 0.389 in. | Intact tablet, smooth shiny surfaces |
| DBDMH/5 wt % Micropro 400 | 5.0 g | 5000 psi | 0.374 in. | Intact tablet, not 100% mold release from top punch |
| DBDMH | 2.5 g | 5000 psi | — | compact shattered and laminated on removal from die |
| CTB product | 2.5 g | 5000 psi | 0.22 in. | Intact tablet |

EXAMPLE 20

The 1,3-dibromo-5,5-dimethylhydantoin/5 wt % MPP-611 tablets produced in Example 18 were placed in glass beakers of water. The tablet appeared to do nothing. Its physical integrity remained intact as it slowly dissolved over a period of several months. In order to prove that it was releasing dissolved halogen, the tablet was removed from the water, washed with deionized water and dried with a paper towel. A plastic wash bottle was then used to wash the tablet into a deionized water solution containing N,N-diethylphenylenediamine (DPD) powder. This solution immediately turned pink when the wash water was introduced, proving that soluble halogen was being washed from the tablet. In this connection, DPD is an indicator of high sensitivity used to detect the presence of soluble halogen at the parts per million level. In the presence of such quantities of dissolved halogen, the DPD turns pink.

EXAMPLE 21

1,3-Dibromo-5,5-dimethylhydantoin was blended with micronized polyethylene wax (MPP-61 1) such that the blend contained 3 wt % of the wax. A sample of the blend (5 g) was introduced to a die made from Hastelloy® C alloy, and compacted to a pressure of 5000 psi. Three more samples (5 g each) were compacted in the same manner, and each time a single tablet was extracted from the die after the pressure had been released. In each case, before filling the die, its interior surfaces were lightly dusted with micronized polypropylene wax to serve as a lubricant. The tablets were manually broken into two equally-sized pieces. One half of each tablet was crushed into a powder with a mortar and pestle, and the powder was titrated to determine its wt % of active bromine. The other half of each tablet was placed in a sealed glass vial and placed in an oven at 50° C. After 30 days, the samples were removed from the oven, ground up, and titrated to determine its wt % of active bromine. For comparative purposes, a control sample of commercially produced 1,3-dibromo-5,5-dimethylhydantoin having an average particle size of about 64.5$\mu$ (containing no micronized polyethylene wax) was subjected to the same operations. In the case of this control sample, it was not possible to extract a single, tablet from the die, and thus only shattered laminates could be tested.

Table 16 lists the results obtained for four samples of 1,3-dibromo-5,5-dimethylhydantoin/3 wt % micronized polyethylene wax blends, along with the control sample containing no additive.

TABLE 16

| | Wt % Active Bromine | |
|---|---|---|
| | Initial | After 30 days |
| Sample 1 | 53.4 | 53.3 |
| Sample 2 | 53.3 | 53.6 |
| Sample 3 | 54.2 | 53.3 |
| Sample 4 | 53.3 | 53,7 |
| Control | 55.3 | 55.2 |

The data in Table 16 indicate that, within the reproducibility, of the analytical technique used, the presence of 3 wt % of micronized polyethylene wax in a 1,3-dibromo-5,5-dimethylhydantoin tablet does not induce a loss of active bromine after storage at 50° C. for 30 days. This absence of active bromine loss demonstrates the chemical compatibility of 1,3-dibromo-5,5-dimethylhydantoin and micronized polyethylene wax.

EXAMPLE 22

The strength of 1,3-dibromo-5,5-dimethylhydantoin tableted with different amounts of micronized polyethylene wax, as described in Example 21, was measured in a series of crush strength tests. In each test, 5 g of blended material was added to a die made from Hastelloy® C alloy and compressed with a screw-driven punch, also made from Hastelloy C alloy, to a pressure of 5000 psi. In each case, before filling the die, the interior surfaces of the die were lightly dusted with micronized polypropylene wax to serve as a lubricant. After extraction of the tablet from the die, a visual observation of the tablet was made.

A Sintech® 1/S compression apparatus equipped with Testworks software was used to determine the crush strength of the tablets. This uses a screw-driven piston,to exert pressure on the tablet until it breaks. The pressure required to reach the breaking point is recorded and reported as the crush strength.

The crush strength of the tablets was compared to a commercial toilet bowl product (abbreviated as CTB product in Table 17). This was purchased from a supermarket, ground to a powder and re-compacted under the conditions described above.

Table 17 summarizes the observations and results. The crush strength data represent an average of 3 separate measurements.

TABLE 17

| Blend | Average thickness | Average crush strength | Observations |
|---|---|---|---|
| DBDMH/5 wt % MPP-611 | 0.38 in. | 93.7 lb./in.* | Single tablets, shiny surfaces, low dust |
| DBDMH/3 wt % MPP-611 | 0.38 in. | 57.9 ib./in. | Single tablets, shiny surfaces, low dust |
| DBDMH/2 wt % MPP-611 | 0.37 in. | 37.0 lb./in. | Single tablets, shiny surface, low dust |
| CTB product | 0.44 in. | 55.2 lb./in. | Single tablets, dull surfaces, dusty |

*An estimate because 2 of the 3 tablets did not break before the limit of the load cell was exceeded.

The data in Table 17 clearly demonstrate that the crush strength of the tablets is a function of the micronized polyethylene wax loading, and that when using micronized polyethylene wax with 1,3-dibromo-5,5-dimethylhydantoin, it is possible to obtain a stronger product than a commercial toilet bowl product.

EXAMPLE 23

A series of different blends was prepared using a variety of micronized waxes (purchased from Micro Powders Incorporated, Tarrytown, N.Y.). Each blend was prepared in the fashion described in Example 17, such that the blend contained 3 wt % wax. The source of the DBDMH used in forming these blends was commercially to produced 1,3-dibromo-5,5-dimethylhydantoin having an average particle size of about 64.5$\mu$. Tableting and crush strength testing were performed as described in Examples 21 and 22.

The crush strength of the tablets was compared to a commercial toilet bowl product (abbreviated as CTB product in Table 18). This commercial toilet bowl product was purchased from a supermarket, ground to a powder, and re-tableted under the conditions described in Example 21.

Table 18 summarizes the observations and results. The crush strength data represent an average of 3 separate measurements.

TABLE 18

| DBDMH blend | Average thickness | Average crush strength | Observations |
|---|---|---|---|
| Polyfluo 200 wax | 0.38 in. | 30.2 lb/in. | Single tablets, tend to end-cap on breaking |
| Polyfluo 400 wax | 0.37 in. | 22.2 lb/in. | Single tablets, tend to end-cap on breaking |
| Micropro 400 wax | 0.36 in. | 11.8 lb/in. | Single tablets, tend to end-cap on breaking |
| Synfluo 180 VF | 0.38 in. | 37.8 lb/in. | Single tablets, tend to end-cap on breaking |
| Polysilk 600 | — | — | Powder is discolored, chemical incompatibility; no tablets were made |
| Handy Tack 140 resin | 0.39 in. | 27.5 lb/in. | Tablets are discolored, chemical incompatibility |
| CTB product | 0.44 in. | 102.3 lb/in. | Single tablets |

Although in the tests summarized in Table 18 the 1,3-dibromo-5,5-dimethylhydantoin tablets were not as strong as the prepared sample of CTB product, nevertheless all of the micronized waxes served as effective binders for 1,3-dibromo-5,5-dimethylhydantoin in that they produced whole tablets that remained intact when extracted from a die, and that exhibited adequate crush strength. However, a micronized modified petroleum resin (Handy Tack 140, Micro Powders Inc., Tarrytown, N.Y.) and a fluorinated hydrocarbon mixture (Polysilk 600, Micro Powders Inc., Tarrytown, N.Y.) both displayed signs of chemical incompatibility with 1,3-dibromo-5,5-dimethylhydantoin.

EXAMPLE 24

Blending and tableting studies were scaled up. A ribbon blender with a volume of two cubic feet was used to mix 25 kg of commercially produced 1,3-dibromo-5,5-dimethylhydantoin, having an average particle size of about 64.5$\mu$, with micronized polyethylene wax (MPP-611) to achieve loadings of 2.0 wt % and 2.5 wt % of wax. The mixing time was 60 minutes in each case. A double-cone, tumble blender with a volume of 5 cubic feet was used to tumble mix 25 kg of 1,3-dibromo-5,5-dimethylhydantoin with micronized polyethylene wax to achieve a loading of 3 wt % of wax. The mixing time was 240 minutes.

Each blend was passed through a Chilsonator® breaker (The Fitzpatrick Company, Elmhurst, Ill.) and a set of screens to produce compacted granules of U.S. mesh size 12 to 18. Virgin, commercially-produced 1,3-dibromo-5,5-dimethylhydantoin having an average particle size of about 64.5 $\mu$, without micronized polyethylene wax, was also passed through the same equipment. This material did not compact and form granules. Instead, material exiting the Chilsonator® was mostly loose powder.

The granules of each 1,3-dibromo-5,5-dimethylhydantoin/micronized polyethylene wax blend were introduced to the feed hopper of a rotary tablet press. The turret contained 18 die cavities, each of which is 0.75 inches in diameter, which was automatically filled with granules and compressed between two punches made of Hastelloy® C alloy. The tablets ejected from the tablet press were collected, and 7 days to later were subject to crush strength testing. The results given in Table 19 are an average of at least 3 tests.

TABLE 19

| DBDMH Blend | Tablet Thickness | Crush strength |
|---|---|---|
| 2 wt % MPP-611, tumble blender | 0.49 in. | 16.6 lb/in |
| 2.5 wt % MPP-611, Ribbon blender | 0.49 in. | 19.3 lb/in |
| 3 wt % MPP-611, Ribbon blender | 0.72 in. | 24.1 lb/in |

The main findings from the runs of Example 24 were that the commercially produced 1,3-dibromo-5,5-dimethylhydantoin with an average particle size of about 64.5$\mu$ alone cannot be compacted into granules suitable for making tablets, and that the presence of micronized polyethylene wax (MPP-611) with such finely-divided 1,3-dibromo-5,5-dimethylhydantoin promotes the process of compaction into granules. These granules can be fed to a tableting machine and compacted into tablets. The strength of the tablets is governed by the amount of micronized polyethylene wax present. The: higher the level of micronized polyethylene wax, the stronger the tablet.

EXAMPLE 25

The crush strength of tablets formed from a large average particle sized 1,3-dibromo-5,5-dimethylhydantoin formulated with a binder was measured. This 1,3-dibromo-5,5-dimethylhydantoin had an average particle size of about 189 microns, and the binder was a micronized polyethylene wax (MPP-611), and the binder was 3 wt % of the blend. The measurements were made utilizing a Sintech 1/S compression apparatus equipped with Testworks software. In these tests the tablets were subjected to increasing force applied along the longitudinal axis of the tablet until breakage occurred. The procedure for producing the tablets was as described in Example 20. The results of the crush strength tests are summarized in Table 20.

TABLE 20

| Tablet Thickness | Crush Strength | Crush Strength |
|---|---|---|
| 0.372 in. | 39.8 lb. | 107.2 lb./in. |
| 0.375 in. | 44.9 lb. | 119.9 lb./in. |
| 0.375 in. | 37.5 lb. | 100.0 lb./in. |
| 0.375 in. | 36.1 lb. | 96.5 lb./in. |
| 0.377 in. | 37.6 lb. | 99.7 lb./in. |
| Averaged Results | 39.2 lb. | 104.6 lb./in. |

The novel large sized 1,3-dibromo-5,5-dimethylhydantoin particulate powders can be produced using process technology described in commonly-owned co-pending application Ser. No. 09/484,844, filed Jan. 18, 2000. In brief, such process comprises, for example, concurrently feeding separate feeds of (i) an aqueous solution or slurry formed from an inorganic base and 5,5-dimethylhydantoin, and (ii) a brominating agent in proportions such that each nitrogen atom is substituted by a bromine atom, thereby continuously forming product which precipitates in an aqueous reaction mixture. The pH of the mixture is continuously maintained in the range of about 5.5 to about 8.5.

As can be seen from the foregoing description, this invention comprises a great number of important embodiments which advance the state of the art. In brief summary, some of these embodiments are as follows:

A) A method of treating water for microbiological control, the method comprising introducing into the water to be treated an amount of 1,3-dibromo-5,5-dimethylhydantoin that is less than the amount of N,N'-bromochloro-5,5-dimethylhydantoin required to achieve the same degree of microbiological control.

B) Individual methods of A) above wherein the 1,3-dibromo-5,5-dimethylhydantoin being used (a) has an average particle size in the range of about 20 to about 600 microns, (b) an average particle size of at least about 175 microns, (c) an average particle size of at least about 200 microns, (d) an average particle size of at least about 300 microns, or (e) an average particle size of at least about 400 microns.

C) Individual methods of A) above wherein the 1,3-dibromo-5,5-dimethylhydantoin being used (i) is in the form of a compacted product produced without a binder, or (ii) is in the form of a compacted product produced using as a binder an amount of a micronized synthetic polyolefin-based hydrocarbon wax and/or a micronized synthetic polyfluorocarbon wax effective to form the compacted product, the wax being compatible with the 1,3-dibromo-5,5-dimethylhydantoin, or (iii) is in the form of a compacted product formed from 1,3-dibromo-5,5-dimethylhydantoin having an average particle size of at least 175 microns, and wherein the compacted product was produced using as a binder an amount of a saturated, normally solid, fatty amide effective to form the compacted product.

D) Individual methods of (i) of C) above wherein the 1,3-dibromo-5,5-dimethylhydantoin being used has an average particle size of at least about 175, at least about 200, at least about 300, or at least about 400, microns.

E) Individual methods of (ii) of C) above wherein the wax is micronized polyethylene wax having, prior to compaction, an average particle size of no greater than about 15 microns, a maximum particle size of no greater than about 40 microns, and a density in the range of about 0.9 to about 1.4 grams per cc at 25° C.; or a micronized polyethylene wax that, prior to compaction, melts at a temperature in the range of about 109° C. to about 111° C.; or a micronized polypropylene wax having, prior to compaction, an average particle size in the range of about 5.0 to about 7.0 microns, a maximum particle size of about 22 microns, and a density in the range of about 0.9 to about 1.4 grams per cc at 25° C.; or a micronized polypropylene wax that melts at a temperature in the range of about 140° C. to about 143° C., that has an average particle size in the range of about 5.0 to about 7.0 microns, and that has a maximum particle size of about 22 microns.

F) Individual methods of (iii) of C) above wherein the 1,3-dibromo-5,5-dimethylhydantoin being used has an average particle size of at least about 200, at least about 300, at least about 400, or at least about 500, microns.

G) A method of combating *Escherichia coli* and/or *Enterococcus faecium* in an aqueous medium, which method comprises introducing into the aqueous medium a biocidally effective amount of 1,3-dibromo-5,5-dimethylhydantoin, preferably wherein the amount is less than the amount of N,N'-bromochloro-5,5-dimethylhydantoin required to achieve the same degree of microbiological control.

H) A method of purveying a microbiological control agent for use in water in accordance with U.S. Environmental Protection Agency regulations, which method comprises purveying a container of a water control agent comprising 1,3-dibromo-5,5-dimethylhydantoin, the container bearing a label having thereon dosage levels pursuant to requirements promulgated by the U.S. Environmental Protection Agency.

I) Individual methods of G) or H) above wherein the 1,3-dibromo-5,5-dimethylhydantoin being used in G) or the control agent being used in H) (i) is in the form of a compacted product produced without a binder, (ii) is in the form of a compacted product produced using as a binder an amount of a micronized synthetic polyolefin-based hydrocarbon wax and/or a micronized synthetic polyfluorocarbon wax effective to form the compacted product, the wax being compatible with the 1,3-dibromo-5,5-dimethylhydantoin, or (iii) is in the form of a compacted product formed from 1,3-dibromo-5,5-dimethylhydantoin having an average particle size of at least 175 microns, and wherein the compacted product was produced using as a binder an amount of a saturated, normally solid, fatty amide effective to form the compacted product.

J) Individual methods of (i) of I) above wherein the 1,3-dibromo-5,5-dimethylhydantoin being used has an average particle size of at least about 175, at least about 200, at least about 300, or at least about 400, microns.

K) Individual methods of (ii) of I) above wherein the wax is polyethylene wax having, prior to compaction, an average particle size of no greater than about 15 microns, a maximum particle size of no greater than about 40 microns, and a density in the range of about 0.9 to about 1.4 grams per cc at 25° C.; or wherein the wax is a polyethylene wax that, prior to compaction, melts at a temperature in the range of about 109° C. to about 111° C.; or wherein the wax is polypropylene wax having, prior to compaction, an average particle size in the range of about 5.0 to about 7.0 microns, a maximum particle size of about 22 microns, and a density in the range of about 0.9 to about 1.4 grams per cc at 25° C.; or wherein the wax, prior to compaction, is a polypropylene wax that melts at a temperature in the range of about 140° C. to about 143° C., that has an average particle size in the range of about 5.0 to about 7.0 microns, and that has a maximum particle size of about 22 microns.

L) Individual methods of (iii) of I) above wherein the 1,3-dibromo-5,5-dimethylhydantoin used in forming the compacted product had an average particle size of at least about 200, at least about 300, or at least about 400, microns.

M) Individual methods of any of A)-G) above wherein the water being treated is (i) recreational water or (ii) industrial cooling water, wastewater, or process water.

N) Individual methods of (i) of M) above wherein the treatment of the water comprises passing a sidestream of the water through a bed of the 1,3-dibromo-5,5- dimethylhydantoin such that a biocidally effective amount of 1,3-dibromo-5,5-dimethylhydantoin is delivered to the water; or comprises dispensing 1,3-dibromo-5,5-dimethylhydantoin from a floating device such that a biocidally effective amount of 1,3-dibromo-5,5-dimethylhydantoin is delivered to the water.

O) A method of (ii) of M) above wherein the treatment of the water comprises passing a sidestream of the water through a bed of the 1,3-dibromo-5,5-dimethylhydantoin such that a biocidally effective amount of 1,3-dibromo-5,5-dimethylhydantoin is delivered to the water.

P) Individual methods of any of H)-L) above wherein the method of introducing the biocidally effective amount of 1,3-dibromo-5,5-dimethylhydantoin comprises passing a sidestream of the water through a bed of the 1,3-dibromo-5,5-dimethylhydantoin such that a biocidally effective amount of 1,3-dibromo-5,5-dimethylhydantoin is delivered to the water; or comprises the method of introducing the biocidally effective amount of 1,3-dibromo-5,5-dimethylhydantoin comprises dispensing 1,3-dibromo-5,5-dimethylhydantoin from a floating device such that a biocidally effective amount of 1,3-dibromo-5,5-dimethylhydantoin is delivered to the water.

Q) Individual methods of H) above wherein the microbiological control agent is purveyed for use in recreational water, or wherein the microbiological control agent is purveyed for use in at least cooling water, wastewater, or process water.

R) A method of treating water to eradicate, substantially eradicate, or reduce biofilm on a surface in contact with the water, which method comprises introducing into the water an amount of 1,3-dibromo-5,5-dimethylhydantoin that is effective to eradicate, substantially eradicate, or at least reduce the biofilm on such surface, such amount preferably being less than the amount of N,N'-bromochloro-5,5-dimethylhydantoin required to achieve the same biofilm eradication or reduction.

S) Individual methods of R) above wherein the 1,3-dibromo-5,5-dimethylhydantoin being used (a) has an average particle size in the range of about 20 to about 600 microns, (b) an average particle size of at least about 175 microns, (c) an average particle size of at least about 200 microns, (d) an average particle size of at least about 300 microns, or (e) an average particle size of at least about 400 microns.

T) Individual methods of R) above wherein the 1,3-dibromo-5,5-dimethylhydantoin being used (i) is in the form of a compacted product produced without a binder, or (ii) is in the form of a compacted product produced using as a binder an amount of a micronized synthetic polyolefin-based hydrocarbon wax and/or a micronized synthetic polyfluorocarbon wax effective to form the compacted product, the wax being compatible with the 1,3-dibromo-5,5-dimethylhydantoin, or (iii) is in the form of a compacted product formed from 1,3-dibromo-5,5-dimethylhydantoin having an average particle size of at least 175 microns, and wherein the compacted product was produced using as a binder an amount of a saturated, normally solid, fatty amide effective to form the compacted product.

U) Individual methods of (i) of T) above wherein the 1,3-dibromo-5,5-dimethylhydantoin being used has an average particle size of at least about 175, at least about 200, at least about 300, or at least about 400, microns.

V) Individual methods of (ii) of T) above wherein the wax is micronized polyethylene wax having, prior to compaction, an average particle size of no greater than about 15 microns, a maximum particle size of no greater than about 40 microns, and a density in the range of about 0.9 to about 1.4 grams per cc at 25° C.; or a micronized polyethylene wax that, prior to compaction, melts at a temperature in the range of about 109° C. to about 111° C.; or a micronized polypropylene wax having, prior to compaction, an average particle size in the range of about 5.0 to about 7.0 microns, a maximum particle size of about 22 microns, and a density in the range of about 0.9 to about 1.4 grams per cc at 25° C.; a micronized polypropylene wax that melts at a temperature in the range of about 140° C. to about 143° C., that has an average particle size in the range of about 5.0 to about 7.0 microns, and that has a maximum particle size of about 22 microns.

W) Individual methods of (iii) of T) above wherein the 1,3-dibromo-5,5-dimethylhydantoin being used has an average particle size of at least about 200, at least about 300, at least about 400, or at least about 500, microns.

X) A method of eradicating, substantially eradicating, or at least reducing *Pseudomonas aeruginosa* biofilm on a surface in contact with an aqueous medium comprising predominately water, which method comprises introducing into the aqueous medium an amount of 1,3-dibromo-5,5-dimethylhydantoin effective to eradicate, substantially eradicate, or at least reduce the *Pseudomonas aeruginosa* biofilm on such surface.

Y) A method of combating *Escherichia coli* and/or *Enterococcus faecium* in an aqueous medium and/or *Pseudomonas aeruginosa* biofilm on a surface in contact with an aqueous medium, which method comprises introducing into the aqueous medium a amount of 1,3-dibromo-5,5-dimethylhydantoin in an amount effective to combat *Escherichia coli* and/or *Enterococcus faecium* in the aqueous medium and/or *Pseudomonas aeruginosa* biofilm on a surface in contact with the aqueous medium, preferably wherein the amount used is less than the amount of N,N'-bromochloro-5,5-dimethylhydantoin required to achieve the same effectiveness against the *Escherichia coli* or the *Enterococcus faecium* or the *Pseudomonas aeruginosa*.

Z) A method of purveying a biofilm control agent for use in water in accordance with U.S. Environmental Protection Agency regulations, which method comprises purveying a container of a biofilm control agent for use in aqueous media, such agent comprising 1,3-dibromo-5,5-dimethylhydantoin, the container bearing a label having thereon dosage levels pursuant to requirements promulgated by the U.S. Environmental Protection Agency.

References herein to biofilm on a surface in contact with an aqueous medium or water, are not to be construed as requiring the aqueous medium or water to be in constant contact with such surface. As long as the aqueous medium or water comes into contact with a surface often enough to result in the formation of biofilm on such surface, it is within the scope of this invention to treat such aqueous medium or water; pursuant to this invention so as to combat such biofilm. For example, this invention includes treatment of aqueous media or water that is splashed, sprayed, or dripped on or against a surface with sufficient frequency for biofilm to develop on such surface. It is also to be understood that the aqueous medium or the water can contain any of a variety of contaminants and/or impurities. The only requirements are that such aqueous medium or water periodically or constantly contacts a surface such that the formation of biofilm occurs on the surface, and that the contaminants and/or impurities in the aqueous medium or water do not prevent the 1,3-dibromo-5,5-dimethylhydantoin from eradicating, or at least reducing the amount of, the biofilm on such surface.

As used herein, including the claims, the term "purveying" means carrying out or causing to be carried out one or more of the following activities: advertising, marketing, promoting for sale, offering for sale, selling, bartering, trading, leasing, merchandising, importing, exporting, dealing in commerce with, supplying, distributing, delivering, and any and all other activities of similar import.

Compounds referred to by chemical name or formula anywhere in this document, whether referred to in the singular or plural, are identified as they exist prior to coming into contact with another substance referred to by chemical name or chemical type (e.g., another component, a solvent, or etc.). It matters not what preliminary chemical changes, if any, take place in the resulting mixture or solution, as such changes are the natural result of bringing the specified substances together under the conditions called for pursuant to this disclosure. Also, even though the claims may refer to substances in the present tense (e.g., "comprises", "is", etc.), the reference is to the substance as it exists at the time just before it is first contacted, blended or mixed with one or more other substances in accordance with the present disclosure.

Except as may be expressly otherwise indicated, the article "a" or "an" if and as used herein is not intended to limit, and should not be construed as limiting, a,:claim to a single element to which the article refers. Rather, the article "a" or "an" if and as used herein is intended to cover one or more such elements, unless the text expressly indicates otherwise.

It will also be understood that the terms "substantial" and "substantially" denote that chemical operations or treatments ordinarily do not involve absolutes. Thus instead of describing a variable or a result as an absolute, it is far more realistic to describe the variable or result as being in the substantial vicinity of the expressed variable or result. For example when describing eradication of an organism, it can be more realistic to refer to the substantial eradication of the organism rather than to imply that absolute total eradication occurs, since one skilled in the art fully realizes that a substantial kill is a very desirable result, and the possibility always exists that even if a small portion of the organism survives the treatment, the overall result is nevertheless highly beneficial in most cases. Thus this document should be read with the application of common sense.

Each and every patent, publication, or commonly-owned patent application referred to in any portion of this specification is incorporated in toto into this disclosure by reference, as if fully set forth herein.

This invention is susceptible to considerable variation in its practice. Therefore the foregoing description is not intended to limit, and should not be construed as limiting, the invention to the particular exemplifications presented hereinabove. Rather, what is intended to be covered is as set forth in the ensuing claims and the equivalents thereof permitted as a matter of law.

That which is claimed is:

1. A method of treating an aqueous medium for microbiological control and/or eradication or reduction of biofilm on a surface in contact with such medium, said method comprising introducing into the aqueous medium to be treated an effective amount of 1,3-dibromo-5,5-dimethylhydantoin that is less than the amount of N,N'-bromochloro-5,5-dimethylhydantoin required to achieve the same degree of effectiveness, wherein the 1,3-dibromo-5,5-dimethylhydantoin used in said treatment is the sole disinfecting agent for sanitizing the aqueous medium, and wherein the 1,3-dibromo-5,5-dimethylhydantoin used:
   a) is in non-compacted form and has an average particle size of at least about 175 microns; or
   b) is in the form of a shape-retentive pressure compacted article devoid of any binder and consists essentially of compacted 1,3-dibromo-5,5-dimethylhydantoin solids having prior to compaction an average particle size of at least about 175 microns; or
   c) is in the form of a shape-retentive pressure compacted article consisting essentially of 1,3-dibromo-5,5-dimethylhydantoin particulate solids and a binder amount of a micronized synthetic polyolefin-based hydrocarbon wax and/or a micronized synthetic polyfluorocarbon wax effective to form said compacted article, said wax being compatible with said 1,3-dibromo-5,5-dimethylhydantoin, or
   d) is in the form of a shape-retentive pressure compacted article consisting essentially of 1,3-dibromo-5,5-dimethylhydantoin particulate solids having prior to compaction, an average particle size of at least about 175 microns, and a binder amount of a saturated, normally solid fatty amide effective to form said compacted article.

2. A method of claim 1 wherein the 1,3-dibromo-5,5-dimethylhydantoin used in said treatment is in non-compacted form and has an average particle size of at least about 175 microns.

3. A method of claim 2 wherein said average particle size is at least about 200 microns.

4. A method of claim 2 wherein said average particle size is at least about 300 microns.

5. A method of claim 1 wherein the 1,3-dibromo-5,5-dimethylhydantoin used in the treatment is in the form of a shape-retentive pressure compacted article consisting essentially of 1,3-dibromo-5,5-dimethylhydantoin particulate solids having, prior to compaction, an average particle size of at least 175 microns, and a binder amount of a saturated, normally solid, fatty amide effective to form said compacted article.

6. A method of claim 5 wherein said average particle size is at least about 200 microns.

7. A method of claim 1 wherein the 1,3-dibromo-5,5-dimethylhydantoin used in the treatment is in the form of a shape-retentive pressure compacted article consisting essentially of 1,3-dibromo-5,5-dimethylhydantoin particulate solids and a binder amount of a micronized synthetic polyolefin-based hydrocarbon wax and/or a micronized synthetic polyfluorocarbon wax effective to form said compacted article, said wax being compatible with said 1,3-dibromo-5,5-dimethylhydantoin.

8. A method of claim 7 wherein the 1,3-dibromo-5,5-dimethylhydantoin particulate solids used in forming said article had, prior to compaction, an average particle size of at least about 175 microns.

9. A method of claim 5 wherein said average particle size is at least about 300 microns.

10. A method of claim 7 wherein said wax is polyethylene ax having, prior to compaction, an average particle size of no greater than about 15 microns, a maximum particle size of no greater than about 40 microns, and a density in the range of about 0.9 to about 1.4 grams per cc at 25° C.

11. A method of claim 7 wherein said wax is a polyethylene wax that melts at a temperature in the range of about 109° C. to about 111° C.

12. A method of claim 7 wherein said wax is polypropylene wax having, prior to compaction, an average particle size in the range of about 5.0 to about 7.0 microns, a maximum particle size of about 22 microns, and a density in the range of about 0.9 to about 1.4 grams per cc at 25° C.

13. A method of claim 7 wherein said wax is a polypropylene wax that melts at a temperature in the range of about 140° C. to about 143° C., that prior to compaction has an average particle size in the range of about 5.0 to about 7.0 microns, and that prior to compaction has a maximum particle size of about 22 microns.

14. A method of claim 2 wherein said average particle size is at least about 400 microns.

15. A method of claim 1 wherein the 1,3,-dibromo-5,5-dimethylhydantoin used in the treatment is in the form of a shape-retentive pressure compacted article devoid of any binder and consists essentially of compacted 1,3-dibromo-5,5-dimethylhydantoin solids having prior to compaction an average particle size of at least about 175 microns.

16. A method of claim 15 wherein said average particle size is at least about 200 microns.

17. A method of claim 15 wherein said average particle size is at least about 300 microns.

18. A method of claim 15 wherein said average particle size is at least about 400 microns.

19. A method of claim 8 wherein said average particle size is at least about 200 microns.

20. A method of claim 8 wherein said average particle size is at least about 300 microns.

21. A method of claim 8 wherein said average particle size is at least about 400 microns.

22. A method of claim 5 wherein said average particle size is at least about 400 microns.

23. A method of combating at least *Escherichia coli* and/or *Enterococcus faecium* in an aqueous medium, which method comprises introducing into said medium a biocidally effective amount of 1,3-dibromo-5,5-dimethylhydantoin that is less than the amount of N,N'-bromochloro-5,5-dimethylhydantoin required to achieve the same degree of effectiveness, wherein the 1,3-dibromo-5,5-dimethylhydantoin used in conducting the method is the sole disinfecting agent for sanitizing the aqueous medium, and wherein the 1,3-dibromo-5,5-dimethylhydantoin used:
   a) is in non-compacted form and has an average particle size of at least about 175 microns, or
   b) is in the form of a shape-retentive pressure compacted article devoid of any binder and consist essentially of compacted 1,3-dibromo-5,5-dimethylhydantoin solids having prior to compaction an average particle size of at least about 175 microns; or
   c) is in the form of a shape-retentive pressure compacted article consisting essentially of 1,3-dibromo-5,5-dimethylhydantoin particulate solids and a binder amount of a micronized synthetic polyolefin-based hydrocarbon wax and/or a micronized synthetic polyfluorocarbon wax effective to form said compacted article, said wax being compatible with said 1,3-dibromo-5,5-dimethylhydantoin, or
   d) is in the form of a shape-retentive pressure compacted article consisting essentially of 1,3-dibromo-5,5-dimethylhydantoin particulate solids having prior to compaction, an average particle size of at least about 175 microns, and a binder amount of a saturated, normally solid fatty amide effective to form said compacted article.

24. A method of eradicating or at least reducing biofilm on a surface contacted by an aqueous medium or water, which method comprises introducing into said medium or water a biocidally effective amount of 1,3-dibromo-5,5-dimethylhydantoin effective to eradicate or at least reduce such biofilm, said amount of 1,3-dibromo-5,5-dimethylhydantoin being less than the amount of N,N'-bromochloro-5,5-dimethylhydantoin required to achieve the same degree of effectiveness, wherein the 1,3-dibromo-5,5-dimethylhydantoin used in conducting the method is the sole disinfecting agent for sanitizing the aqueous medium, and wherein the 1,3-dibromo-5,5-dimethylhydantoin used:
   a) is in non-compacted form and has an average particle size of at least about 175 microns; or
   b) is in the form of a shape-retentive pressure compacted article devoid of any binder and consists essentially of compacted 1,3-dibromo-5,5-dimethylhydantoin solids having prior to compaction an average particle size of at least about 175 microns; or
   c) is in the form of a shape-retentive pressure compacted article consisting essentially of 1,3-dibromo-5,5-dimethylhydantoin particulate solids and a binder amount of a micronized synthetic polyolefin-based hydrocarbon wax and/or a micronized synthetic polyfluorocarbon wax effective to form said compacted article, said wax being compatible with said 1,3-dibromo-5,5-dimethylhydantoin, or
   d) is in the form of a shape-retentive pressure compacted article consisting essentially of 1,3-dibromo-5,5-dimethylhydantoin particulate solids having prior to compaction, an average particle size of at least about 175 microns, and a binder amount of a saturated, normally solid fatty amide effective to form said compacted article.

25. A method of eradicating or reducing at least *Pseudomonas aeruginosa* biofilm on a surface contacted by an aqueous medium or water, which method comprises introducing into the aqueous medium or water a biocidally effective amount of 1,3-dibromo-5,5-dimethylhydantoin effective to eradicate or at least reduce such biofilm, said amount of 1,3-dibromo-5,5-dimethylhydantoin being less than the amount of N,N'-bromochloro-5,5-dimethylhydantoin required to achieve the same degree of effectiveness, wherein the 1,3-dibromo-5,5-dimethylhydantoin used in conducting the method is the sole disinfecting agent for sanitizing the aqueous medium, and wherein the 1,3-dibromo-5,5-dimethylhydantoin used:
   a) is in non-compacted form and has an average particle size of at least about 175 microns; or
   b) is in the form of a shape-retentive pressure compacted article devoid of any binder and consists essentially of compacted 1,3-dibromo-5,5-dimethylhydantoin solids having prior to compaction an average particle size of at least about 175 microns; or
   c) is in the form of a shape-retentive pressure compacted article consisting essentially of 1,3-dibromo-5,5-dimethylhydantoin particulate solids and a binder amount or a micronized synthetic polyolefin-based hydrocarbon wax and/or a micronized synthetic polyfluorocarbon wax effective to form said compacted article, said wax being compatible with said 1,3-dibromo-5,5-dimethylhydantoin, or
   d) is in the form of a shape-retentive pressure compacted article consisting essentially of 1,3-dibromo-5,5-dimethylhydantoin particulate solids having prior to compaction, an average particle size of at least about 175 microns, and a binder amount of a saturated, normally solid fatty amide effective to form said compacted article.

26. A method of claim 1 wherein biofilm on a surface is eradicated or at least reduced by contacting said biofilm with an aqueous medium or water into which an amount of 1,3-dibromo-5,5-dimethylhydantoin effective to eradicate or at least reduce such biofilm has been introduced, and wherein said contacting is for one or more periods long enough to eradicate or at least reduce said biofilm.

27. A method of claim 1 wherein the aqueous medium treated is:

i) recreational water and wherein the treatment of the water comprises (A) passing a sidestream of the water through a bed of the 1,3-dibromo-5,5-dimethylhydantoin such that a biocidally effective amount of 1,3-dibromo-5,5-dimethylhydantoin is delivered to the water, or (B) dispensing 1,3-dibromo-5,5-dimethylhydantoin from a floating device such that a biocidally effective amount of 1,3-dibromo-5,5-dimethylhydantoin is delivered to the water; or ii) industrial cooling water, wastewater, or process water and wherein the treatment of the water comprises passing a side stream of the water through a bed of the 1,3-dibromo-5,5-dimethylhydantoin such that a biocidally effective amount of 1,3-dibromo-5,5-dimethylhydantoin is delivered to the water.

28. A method of claim 26 wherein said biofilm comprises at least *Pseudomonas aeruginosa* biofilm on said surface.

29. A method of claim 1 wherein said 1,3-dibromo-5,5-dimethylhydantoin is continuously or periodically dispensed into the aqueous medium in an amount effective to concurrently eradicate or at least reduce biofilm on surfaces contacted by such aqueous medium or water, and to effect microbiological control of microbial species present in said aqueous medium or water.

30. A method of claim 29 wherein the treatment of the aqueous medium or water comprises dispensing 1,3-dibromo-5,5-dimethylhydantoin into a sidestream of the aqueous medium or water, and flowing the resultant treated sidestream into a larger body of the aqueous medium or water.

31. A method of claim 29 wherein the treatment of the water comprises dispensing 1,3-dibromo-5,5-dimethylhydantoin from a floating device such that a biocidally effective amount of 1,3-dibromo-5,5-dimethylhydantoin is delivered to the water.

32. A method of claim 29 wherein the water being treated is recreational water, industrial cooling water, wastewater, or process water.

33. A method of claim 24 wherein said biofilm comprises extra-cellular polysaccharide.

34. A method of claim 33 wherein said biofilm harbors at least one pathogen.

* * * * *